(12) United States Patent
Shin et al.

(10) Patent No.: US 8,377,899 B2
(45) Date of Patent: Feb. 19, 2013

(54) COMPOSITION FOR TREATMENT OF CERVIX CANCER

(75) Inventors: Young Kee Shin, Seoul (KR); Hun Soon Jung, Seoul (KR); Yu Kyoung Oh, Seoul (KR)

(73) Assignee: SNU R&DB Foundation (KR)

( * ) Notice: Subject to any disclaimer, the term of this patent is extended or adjusted under 35 U.S.C. 154(b) by 706 days.

(21) Appl. No.: 12/513,337

(22) PCT Filed: Nov. 5, 2007

(86) PCT No.: PCT/KR2007/005548
§ 371 (c)(1),
(2), (4) Date: May 1, 2009

(87) PCT Pub. No.: WO2008/054184
PCT Pub. Date: May 8, 2008

(65) Prior Publication Data
US 2010/0062051 A1    Mar. 11, 2010

(30) Foreign Application Priority Data

Nov. 3, 2006 (KR) .......................... 10-2006-0108352

(51) Int. Cl.
*C12N 15/113* (2010.01)

(52) U.S. Cl. ...................................... 514/44 A; 424/417

(58) Field of Classification Search ................. 514/44 A; 424/417
See application file for complete search history.

(56) References Cited

FOREIGN PATENT DOCUMENTS

| EP | 1 439 227 A1 | 7/2004 |
|---|---|---|
| WO | WO 2006/014729 A2 | 2/2006 |
| WO | WO 2006/035974 * | 6/2006 |

OTHER PUBLICATIONS

Putral et al. (Nov. 1, 2005) Mol. Pharmacol.*
Shimizu et al. (1998) J. Clin. Oncol., vol. 16(5), 1869-1878.*
Sorensen et al. (2003) J. Mol. Biol., vol. 327, 761-766.*
Shimizu et al. (1998) J. Clin. Oncol., vol. 16, 1869-1878.*
Jiang et al. "Selective Silencing of Viral Gene E6 and E7 Expression in HPV-Positive Human Cervical Carcinoma Cells Using Small Interfering RNAs," *Methods in Molecular Biology*, vol. 292:401-420 (2005).
Fujii et al. "Intratumor injection of small interfering RNA-targeting human papillomavirus 18 E6 and E7 successfully inhibits the growth of cervical cancer," *International Journal of Oncology*, vol. 29:541-548 (2006).
Niu et al. "Inhibition of HPV 16 E6 oncogene expression by RNA interference in vitro and in vivo," *Int. J. Gynecol. Cancer*, vol. 16:743-751 (2006).

* cited by examiner

*Primary Examiner* — Anne Marie S Wehbe
(74) *Attorney, Agent, or Firm* — Klarquist Sparkman, LLP

(57) ABSTRACT

The present invention relates to a composition for the treatment of cervix cancer, more precisely a composition for the treatment of cervix cancer comprising the first active part containing human papilloma virus (referred as "HPV" hereinafter) specific siRNA as an active ingredient and the second active part containing an anticancer agent as an active ingredient. The composition for the treatment of cancer of the present invention has better anticancer effect than the single therapy of the HPV specific siRNA or the anticancer agent, and has an advantage of reducing side effects by using the anticancer agent at a low concentration.

12 Claims, 23 Drawing Sheets single therapy

A.

B.

C.

D.

E.

combination therapy

F.

G.

H.

I.

use of oligofectamine

A.

B.

C.

SEQUENCE LISTING

```
<160> NUMBER OF SEQ ID NOS: 15

<210> SEQ ID NO 1
<211> LENGTH: 19
<212> TYPE: DNA
<213> ORGANISM: Artificial Sequence
<220> FEATURE:
<223> OTHER INFORMATION: HPV18E6-1 siRNA target sequence

<400> SEQUENCE: 1
```

-continued

```
taacctgtgt atattgcaa                                               19

<210> SEQ ID NO 2
<211> LENGTH: 19
<212> TYPE: DNA
<213> ORGANISM: Artificial Sequence
<220> FEATURE:
<223> OTHER INFORMATION: HPV18E6-2 siRNA target sequence

<400> SEQUENCE: 2
ctaactaaca ctgggttat                                               19

<210> SEQ ID NO 3
<211> LENGTH: 19
<212> TYPE: DNA
<213> ORGANISM: Artificial Sequence
<220> FEATURE:
<223> OTHER INFORMATION: HPV16E6 siRNA target sequence

<400> SEQUENCE: 3
accgttgtgt gatttgtta                                               19

<210> SEQ ID NO 4
<211> LENGTH: 19
<212> TYPE: DNA
<213> ORGANISM: Artificial Sequence
<220> FEATURE:
<223> OTHER INFORMATION: HPV16E6 siRNA target sequence

<400> SEQUENCE: 4
aaagagaact gcaatgttt                                               19

<210> SEQ ID NO 5
<211> LENGTH: 19
<212> TYPE: DNA
<213> ORGANISM: Artificial Sequence
<220> FEATURE:
<223> OTHER INFORMATION: HPV31E6 siRNA target sequence

<400> SEQUENCE: 5
aaaggtcagt taacagaaa                                               19

<210> SEQ ID NO 6
<211> LENGTH: 19
<212> TYPE: DNA
<213> ORGANISM: Artificial Sequence
<220> FEATURE:
<223> OTHER INFORMATION: HPV33E6 siRNA target sequence

<400> SEQUENCE: 6
aacgacatgt ggatttaaa                                               19

<210> SEQ ID NO 7
<211> LENGTH: 19
<212> TYPE: DNA
<213> ORGANISM: Artificial Sequence
<220> FEATURE:
<223> OTHER INFORMATION: HPV35E6 siRNA target sequence

<400> SEQUENCE: 7
ccagctgaac gaccttaca                                               19

<210> SEQ ID NO 8
<211> LENGTH: 19
<212> TYPE: DNA
<213> ORGANISM: Artificial Sequence
<220> FEATURE:
```

```
-continued

<223> OTHER INFORMATION: HPV45E6 siRNA target sequence

<400> SEQUENCE: 8
atatgctgca tgccataaa                                                19

<210> SEQ ID NO 9
<211> LENGTH: 19
<212> TYPE: DNA
<213> ORGANISM: Artificial Sequence
<220> FEATURE:
<223> OTHER INFORMATION: HPV52E6-1 siRNA target sequence

<400> SEQUENCE: 9
gaagagaggt atacaagtt                                                19

<210> SEQ ID NO 10
<211> LENGTH: 19
<212> TYPE: DNA
<213> ORGANISM: Artificial Sequence
<220> FEATURE:
<223> OTHER INFORMATION: HPV52E6-2 siRNA target sequence

<400> SEQUENCE: 10
caaacaagcg atttcataa                                                19

<210> SEQ ID NO 11
<211> LENGTH: 19
<212> TYPE: DNA
<213> ORGANISM: Artificial Sequence
<220> FEATURE:
<223> OTHER INFORMATION: HPV56E6 siRNA target sequence

<400> SEQUENCE: 11
taacacgtgc tgaggtata                                                19

<210> SEQ ID NO 12
<211> LENGTH: 19
<212> TYPE: DNA
<213> ORGANISM: Artificial Sequence
<220> FEATURE:
<223> OTHER INFORMATION: HPV56E6-2 siRNA target sequence

<400> SEQUENCE: 12
agatgtcaaa gtccgttaa                                                19

<210> SEQ ID NO 13
<211> LENGTH: 19
<212> TYPE: DNA
<213> ORGANISM: Artificial Sequence
<220> FEATURE:
<223> OTHER INFORMATION: HPV58E6-1 siRNA target sequence

<400> SEQUENCE: 13
ccacggacat tgcatgatt                                                19

<210> SEQ ID NO 14
<211> LENGTH: 21
<212> TYPE: DNA
<213> ORGANISM: Artificial Sequence
<220> FEATURE:
<223> OTHER INFORMATION: HPV58E6-2 siRNA target sequence

<400> SEQUENCE: 14
tgcttacgat tgctatctaa a                                             21

<210> SEQ ID NO 15
```

```
<211> LENGTH: 21
<212> TYPE: DNA
<213> ORGANISM: Artificial Sequence
<220> FEATURE:
<223> OTHER INFORMATION: GFP siRNA sequence

<400> SEQUENCE: 15
ggctacgtcc aggagcgcac c                                              21
```

COMPOSITION FOR TREATMENT OF CERVIX CANCER

CROSS REFERENCE TO RELATED APPLICATIONS

This is the U.S. National Stage of International Application No. PCT/KR2007/005548, filed Nov. 5, 2007, which was published in English under PCT Article 21(2), which in turn claims the benefit of Korean Patent Application No. 10-2006-0108352, filed Nov. 3, 2006. Both applications are incorporated by reference herein in their entirety.

TECHNICAL FIELD

The present invention relates to a composition for the treatment of cervix cancer, more precisely a composition for the treatment of cervix cancer comprising the first active part containing human papilloma virus (referred as "HPV" hereinafter) specific siRNA as an active ingredient and the second active part containing an anticancer agent as an active ingredient.

BACKGROUND ART

Cervix cancer is one of the most frequent malignant tumors in women. Incidence of invasive cervix cancer is slowly decreasing, but it is still one of the most frequent cancers that takes 25% of total woman cancer in the developmental countries (Harro et al, *J Natl Cancer Inst* 93(4):284-292, 2001).

Clinical and molecular epidemiological studies say human papilloma virus (referred as "HPV" hereinafter) infection is the major cause of cervix cancer (Brisson et al, *Am J Epidemiol* 140(8):700-710, 1994; Schiffman et al, *J Natl Cancer Inst* 85(12):958-964, 1993). HPV is a small DNA virus composed of approximately 8000 nucleotides and causing benign and malignant tumors. Up to date, 100 or more HPV subtypes have been classified according to genome and genotypes of approximately 90 HPV subtypes have been completely analyzed. Among these, high risk HPV types (for example, HPV-16, 18, 31, 33, 35, 45, 51, 52 and 56) are involved in almost 90% of cervix cancer cases. Among cervix cancers caused by HPV infection, at least 50% are associated with HPV-16, and HPV-18 (12%), HPV-45 (8%), and HPV-31 (5%) follow (Munoz and Bosch, *Salud Publica Mex* 39(4):274-282, 1997).

HPV encodes two oncoproteins, protein E6 and protein E7, which are involved in cell immortalization and transformation via HPV. Oncoprotein E6 is bound to tumor suppressor protein p53 to decompose the p53 through ubiquitin pathway. In the meantime, oncoprotein E7 is directly bound to Rb to induce hyper-phosphorylation (Dyson et al, *Science* 243(4893):934-937, 1989; Huibregtse et al, *Mol Cell Biol* 13(2):775-784, 1993a; Huibregtse et al, *Mol Cell Biol* 13(8):4918-4927, 1993b; Munger et al, *Embo J* 8(13):4099-4105, 1989). First, protein E6 forms a complex with E6-AP (E6-associated protein) that is E3 ubiquitin-protein ligase. Then, the E6/E6-AP complex is combined with wild type p53 to induce ubiquitination, suggesting that the complex interrupts p53 mediated cell response to DNA damage.

The tumor suppressor protein p53 is regulated by Mdm2-mediated ubiquitination. However, in the case of cervix cancer with HPV infection, p53 decomposition is accomplished by ubiquitination mediated not by Mdm2 but by E6 (Hengstermann et al, *Proc Natl Acad Sci U S A* 98(3):1218-1223, 2001).

Therefore, unlike many other cancers, cervix cancer with HPV infection exhibits has wild type p53 gene (Hainaut et al, *Nucleic Acids Res* 26(1):205-213, 1998; Scheffner et al, *Proc Natl Acad Sci U S A* 88(13):5523-5527, 1991). However, the expression level of the protein p53 therein is very low because it is decomposed by protein E6.

In particular, HPV E6 is a promising target for the treatment of cervix cancer. Approaches targeting E6 or E6/E6-AP complex result in various treatment methods.

For example, attempts using cytotoxic agents, anti-viral agents releasing Zn of the oncoprotein E6, epitope-peptides (mimotope) of E6-AP, anti-E6 lybozymes, peptide aptarmers targeting the viral oncoprotein E6, siRNAs targeting the viral oncoprotein E6 gene, and co-use thereof, etc (Beerheide et al, *J Natl Cancer Inst* 91(14):1211-1220, 1999; Beerheide et al, *Bioorg Med Chem* 8(11):2549-2560, 2000; Butz et al, *Proc Natl Acad Sci USA* 97(12):6693-6697, 2000; Butz et al, *Oncogene* 22(38):5938-5945, 2003; Jiang and Milner, *Oncogene* 21(39):6041-6048, 2002; Liu et al, *Biochemistry* 43(23):7421-7431, 2004; Wesierska-Gadek et al, *Int J Cancer* 101(2):128-136, 2002; Yoshinouchi et al, *Mol Ther* 8(5):762-768, 2003; Zheng et al, *Di Yi Jun Yi Da Xue Xue Bao* 22(6):496-498, 2002) have been made.

It has been recently proved that siRNA not only can silence a specific endogenous gene selectively in animal cells (Sui et al, *Proc Natl Acad Sci U S A* 99(8):5515-5520, 2002; Yu et al, *Proc Natl Acad Sci U S A* 99(9):6047-6052, 2002) but also can silence a viral gene in the case of the virus mediated disease (Ge et al, *Proc Natl Acad Sci U S A* 100(5):2718-2723, 2003; Kitabwalla and Ruprecht, *N Engl J Med* 347(17):1364-1367, 2002; Milner, *Expert Opin Biol Ther* 3(3):459-467, 2003).

RNA interfering induced by siRNA transfection draws our attention as a new therapeutic method for virus infection in human.

siRNA that targets E6 and E7 in cervix cancer cells infected with HPV accumulates p53 and pRb, leading to apoptosis or senescence. RNAi targeting E6 and E7 has been confirmed to silence the expressions of these proteins in the cervix cancer cell line infected with HPV-16 (Jiang and Milner, *Oncogene* 21(39):6041-6048, 2002; Putral et al, *Mol Pharmacol* 68(5):1311-1319, 2005; Yoshinouchi et al, *Mol Ther* 8(5):762-768, 2003) and in the cell line infected with HPV-18 (Butz et al, *Oncogene* 22(38):5938-5945, 2003; Gu et al, *Cancer Gene Ther,* 2006; Hall and Alexander, *J Virol* 77(10):6066-6069, 2003). In spite of the above results, the methods are still in the middle of controversy because they cause low growth, senescence or apoptosis.

A paper describing combination therapy of chemotherapy using cisplatin and radiotherapy was published in 1999 (Thomas G M, *N Engl J Med.* 340(15):1198-1200, 1999). This method could significantly improve survival rate of women with severe local cervix cancer. Cisplatin is a DNA damaging drug which is widely used for the treatment of ovarian cancer, cervix cancer, head cancer, neck cancer, non-small cell lung cancer, etc. Most recently, the mechanism of this drug was precisely investigated based on platinum. However, the mechanism including the processes of absorption and excretion of the drug, signal transduction of DNA damage, cell cycle arrest, DNA repair and apoptosis has not been disclosed, yet (Wang and Lippard, *Nat Rev Drug Discov* 4(4):307-320, 2005).

In HPV-18 HeLa cells, after the treatment with cisplatin, p53 is released from the E6 mediated degradation pathway and preferentially accumulated in nucleus (Wesierska-Gadek et al, *Int J Cancer* 101(2):128-136, 2002). In HPV-16 SiHa cells, combination therapy of radiotherapy and cisplatin results in the recovery of p53 functions, so that sensitivity to radiation is increased (Huang et al, *J Cell Biochem* 91(4):756-765, 2004).

In cells infected with high risk HPV, combination therapy of siRNA targeting E6 and chemotherapy with cisplatin or radiotherapy is expected to bring cytotoxic effect, based on the theory that E6 siRNA acts as an effective chemical or radiation sensitizer.

However, other researches showed such results that the transcript that does not have 100% complementarity with siRNA can also induce gene silencing by RNA interference (Fedorov et al, *Rna* 12(7):1188-1196, 2006), which is called "off-target effect". That is, RNA interference is not authentically specific to a target, so that non-target genes can be silenced according to the concentration of siRNA. Nevertheless, no previous studies have reported such off-target effect when they carried out experiments with siRNA against HPV.

Therefore, the present inventors completed this invention by confirming that combination therapy of siRNA having the sequence specific to HPV E6 and low concentration of cisplatin could result in anticancer effect in cervix cancer cells.

DISCLOSURE

Technical Problem

It is an object of the present invention to provide a composition for the treatment of cancer comprising the first active part containing human papilloma virus specific siRNA as an active ingredient and the second active part containing an anticancer agent at a low concentration as an active ingredient, a preparing method thereof and a treatment method using the same.

Technical Solution

To achieve the above object, the present invention provides a composition for the treatment of cancer comprising the first active part containing human papilloma virus (referred as "HPV" hereinafter) specific siRNA as an active ingredient and the second active part containing an anticancer agent at a low concentration as an active ingredient.

The present invention also provides a preparing method of the composition for the treatment of cancer.

The present invention further provides a treatment method of cancer using the composition for the treatment of cancer.

Advantageous Effect

The composition for the treatment of cancer of the present invention comprising the first active part containing human papilloma virus (referred as "HPV" hereinafter) specific siRNA as an active ingredient and the second active part containing an anticancer agent at a low concentration as an active ingredient has an excellent cancer treatment effect, compared with the treatment with HPV specific siRNA alone or a single anticancer agent. According to the present invention, side-effects caused by using high concentration of anticancer agent can be reduced because low concentration of anticancer agent is used in this invention.

DESCRIPTION OF DRAWINGS

The application of the preferred embodiments of the present invention is best understood with reference to the accompanying drawings, wherein.

A: 18E6-1 siRNA;
B: 18E6-2 siRNA;
C: GFP siRNA+low Cisplatin;
D: 18E6-1 siRNA+low Cisplatin; and
E: 18E6-2 siRNA+low Cisplatin.

Figure 15:
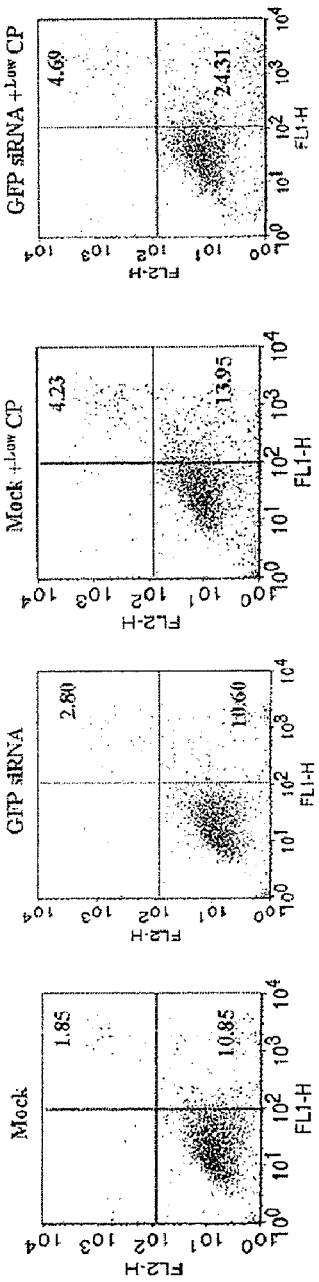
Figure 15:
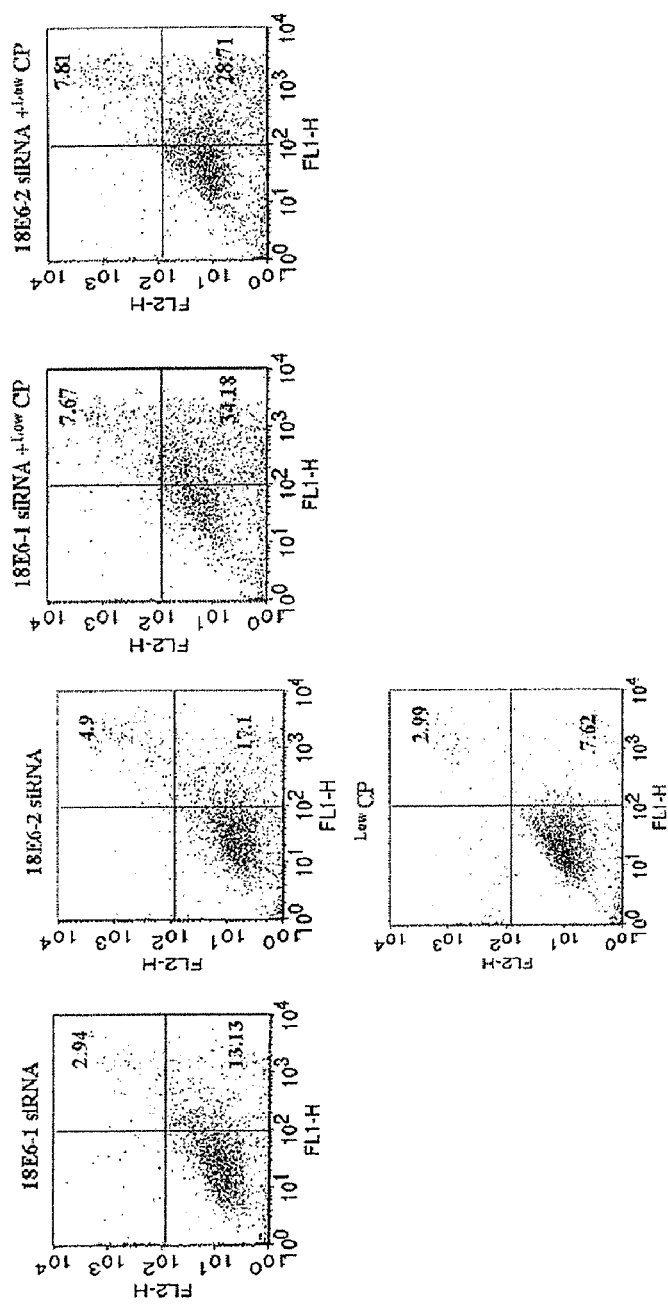

FIG. 15 is a graph illustrating the apoptosis of the group with single therapy and the group with combination therapy on the 7$^{th}$ day of culture.

Figure 16:
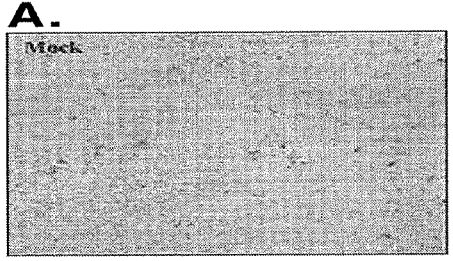
Figure 16:
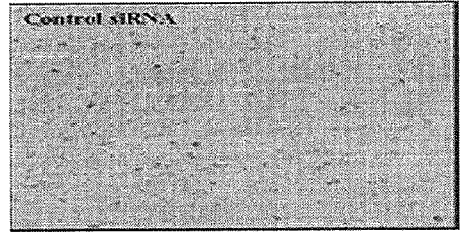
Figure 16:
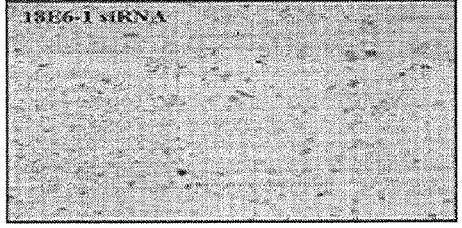
Figure 16:
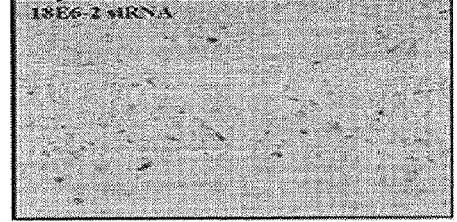
Figure 16:
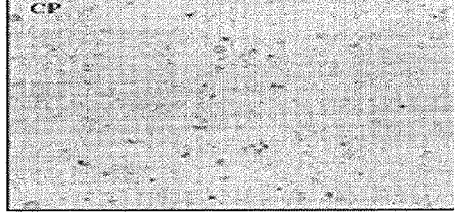
Figure 16:
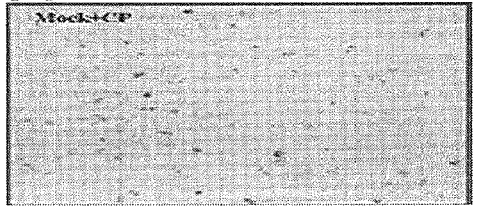
Figure 16:
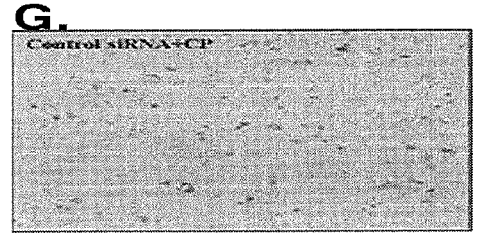
Figure 16:
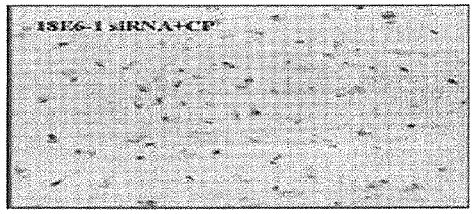
Figure 16:
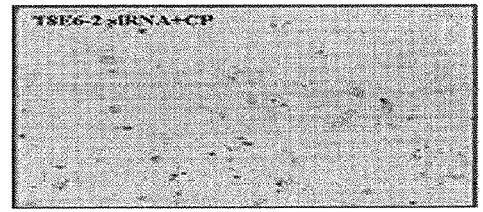

FIG. 16 is a photograph illustrating the senescence of the group with single therapy and the group with combination therapy on the 7$^{th}$ day of culture:
A: Mock;
B: control siRNA;
C: 18E6-1 siRNA;
D: 18E6-2 siRNA;
E: low Cisplatin;
F: Mock+low Cisplatin;
G: control siRNA+low Cisplatin;
H: 18E6-1 siRNA+low Cisplatin; and
I: 18E6-2 siRNA+low Cisplatin.

Figure 17:
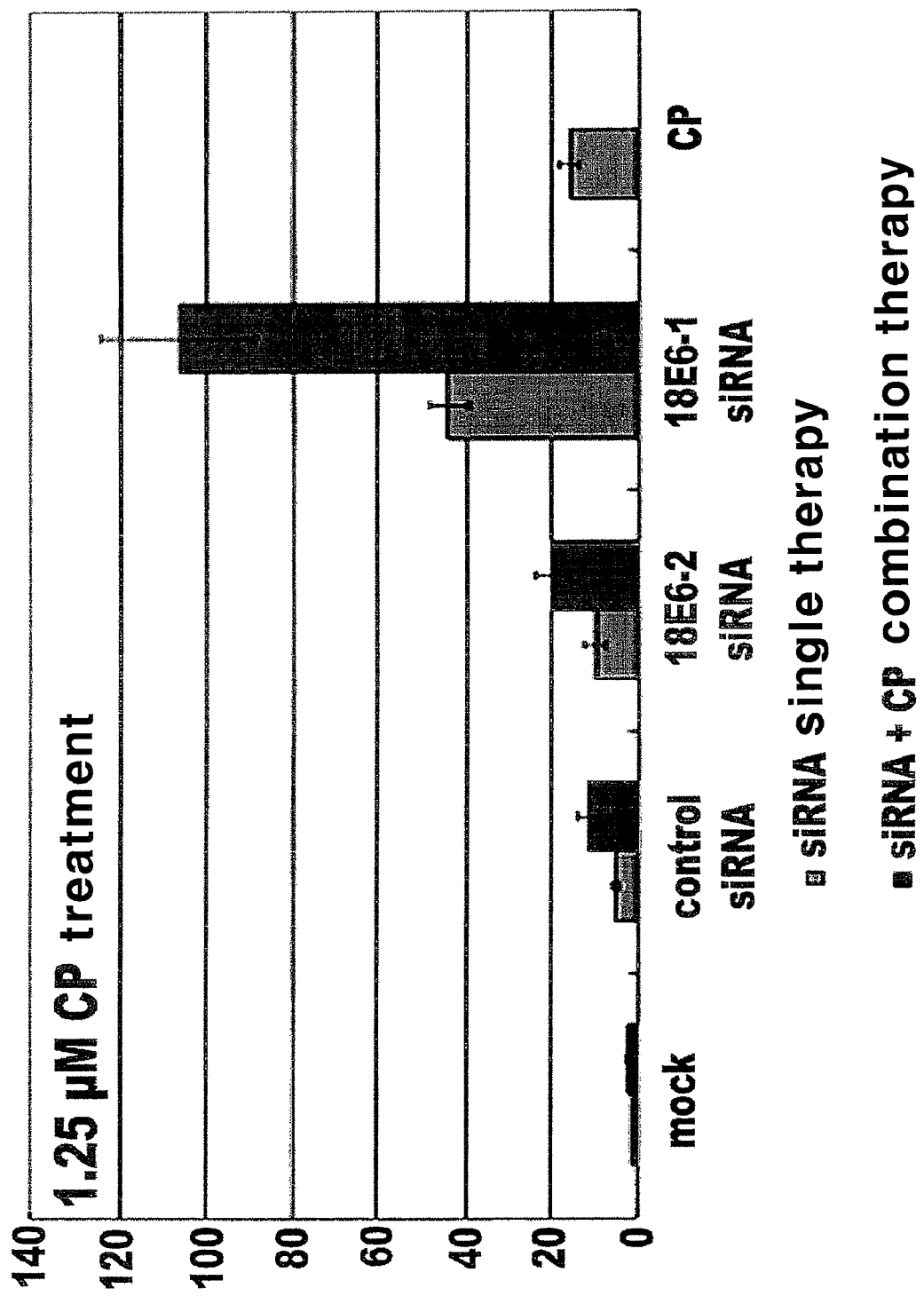

FIG. 17 is a graph illustrating the number of cells showing senescence of the group with single therapy and the group with combination therapy on the 7$^{th}$ day of culture.

Figure 18:
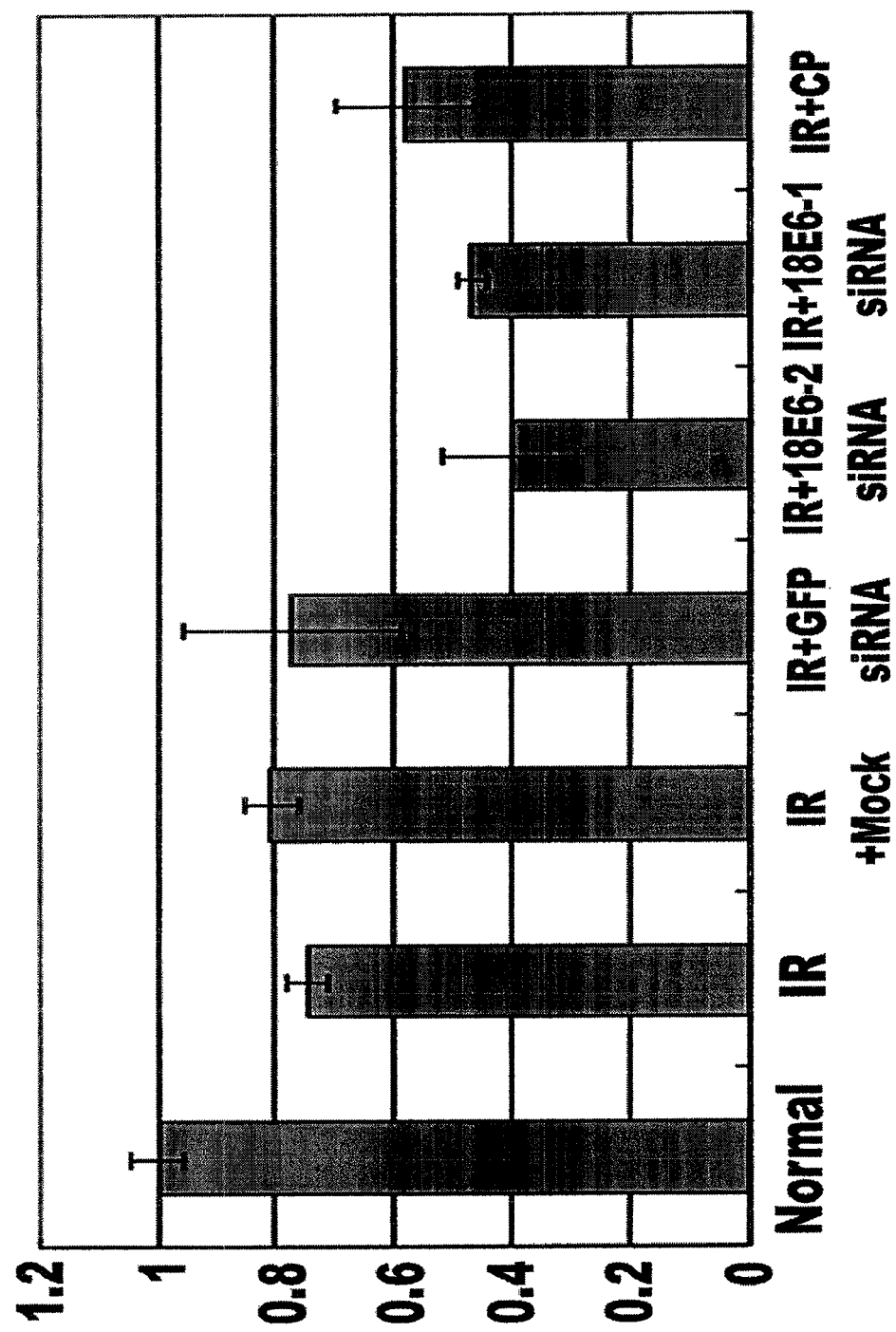

FIG. 18 is a graph illustrating the number of HeLa cells survived from combination therapy of radiotherapy and siRNA.

Figure 19:
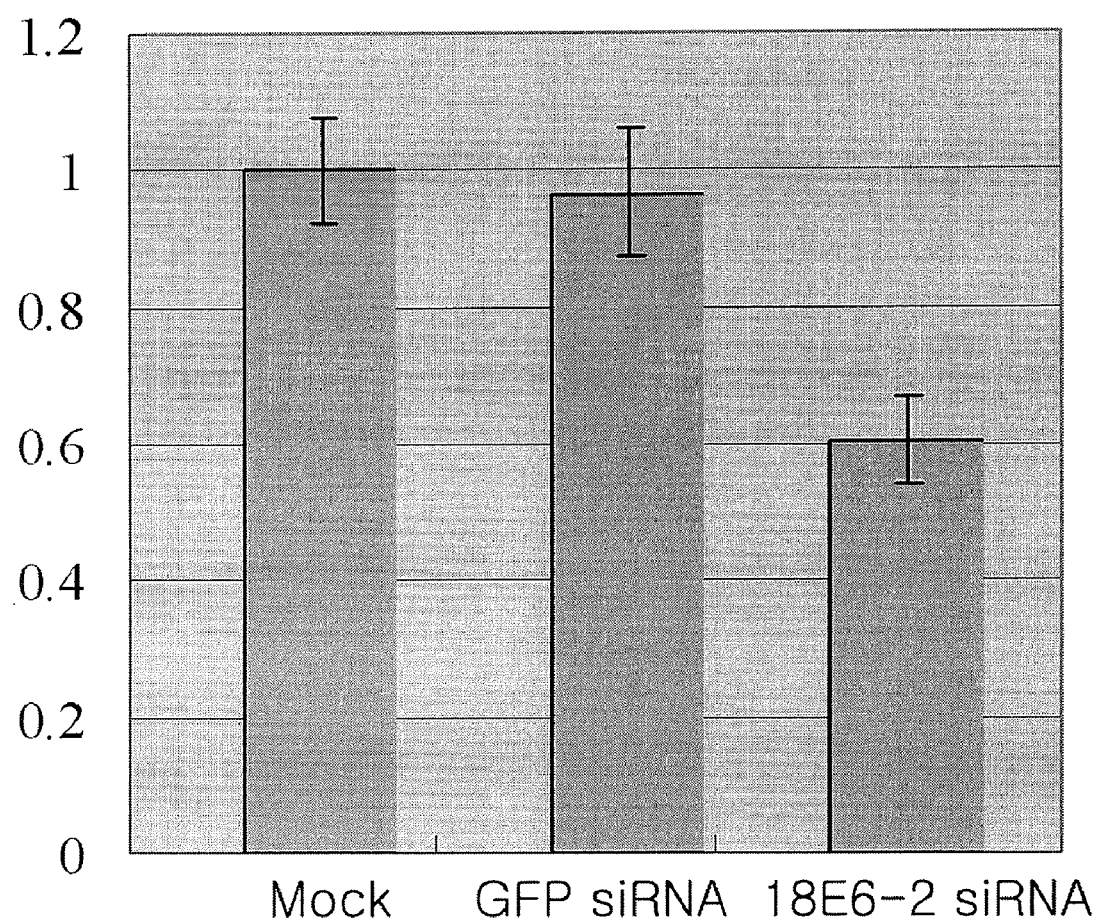

FIG. 19 is a graph illustrating the evaluation of the transfer rate of 18E6 siRNA by drug delivery system, for which liposome containing 18E6 siRNA was injected into cells and the cell survival rate was measured.

Figure 20:
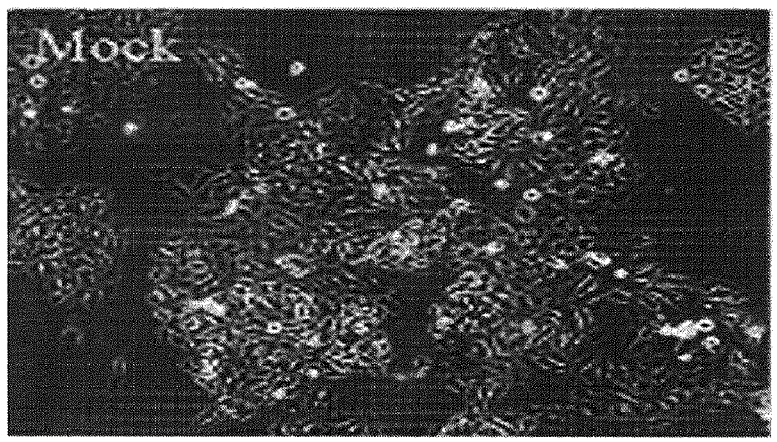
Figure 20:
Figure 20:
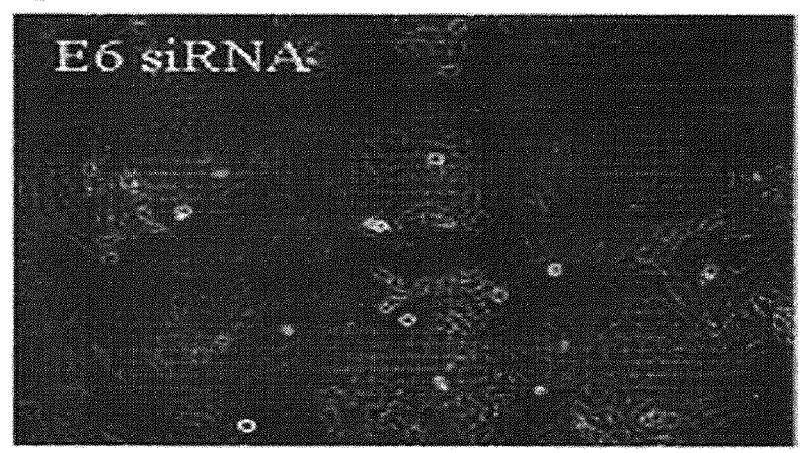

FIG. 20 is a photograph illustrating the evaluation of the transfer rate of 18E6 siRNA by drug delivery system, for which liposome containing 18E6 siRNA was injected into cells and the cell morphology was observed:
A: Mock;
B: GFP siRNA; and
C: E6 siRNA.

Figure 21:
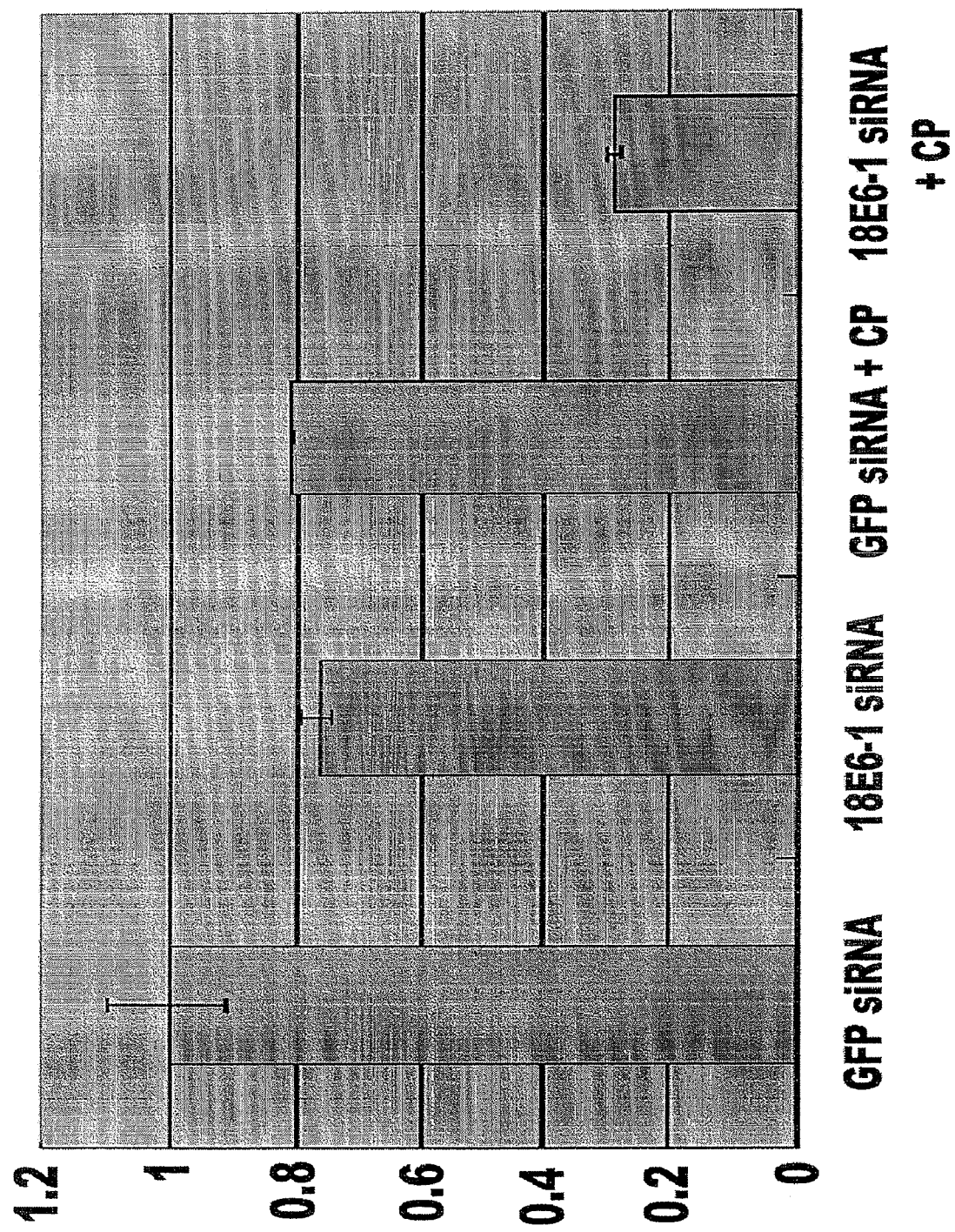

FIG. 21 illustrates the cell number after combination therapy with GFP siRNA, 18E6-1 siRNA and cisplatin in HeLa-Luc cell line.

Figure 22:
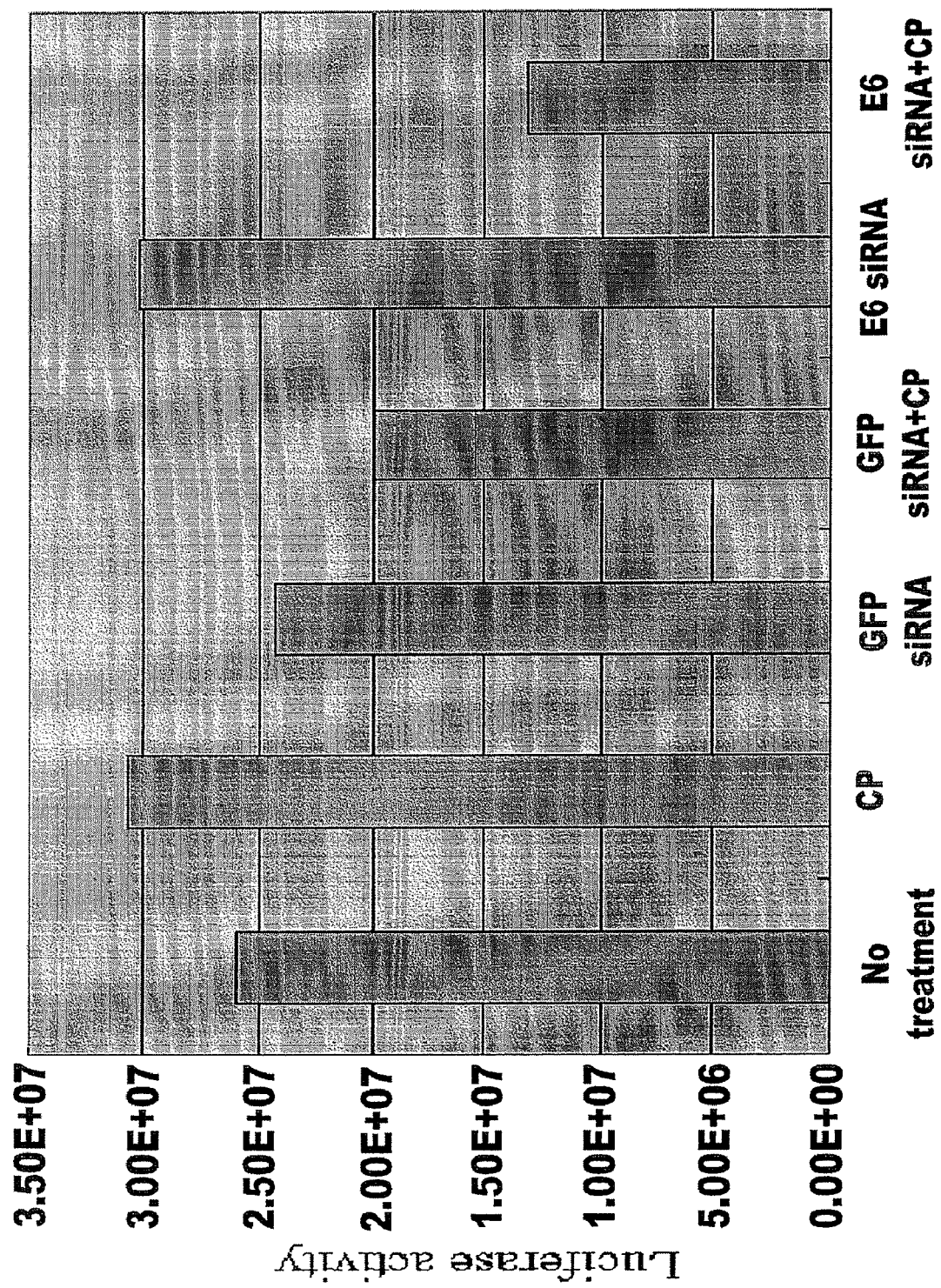

FIG. 22 is a graph illustrating the changes of the tumor size in the animal xenograft model after combination therapy with GFP siRNA, E6 siRNA and cisplatin.

Figure 23:
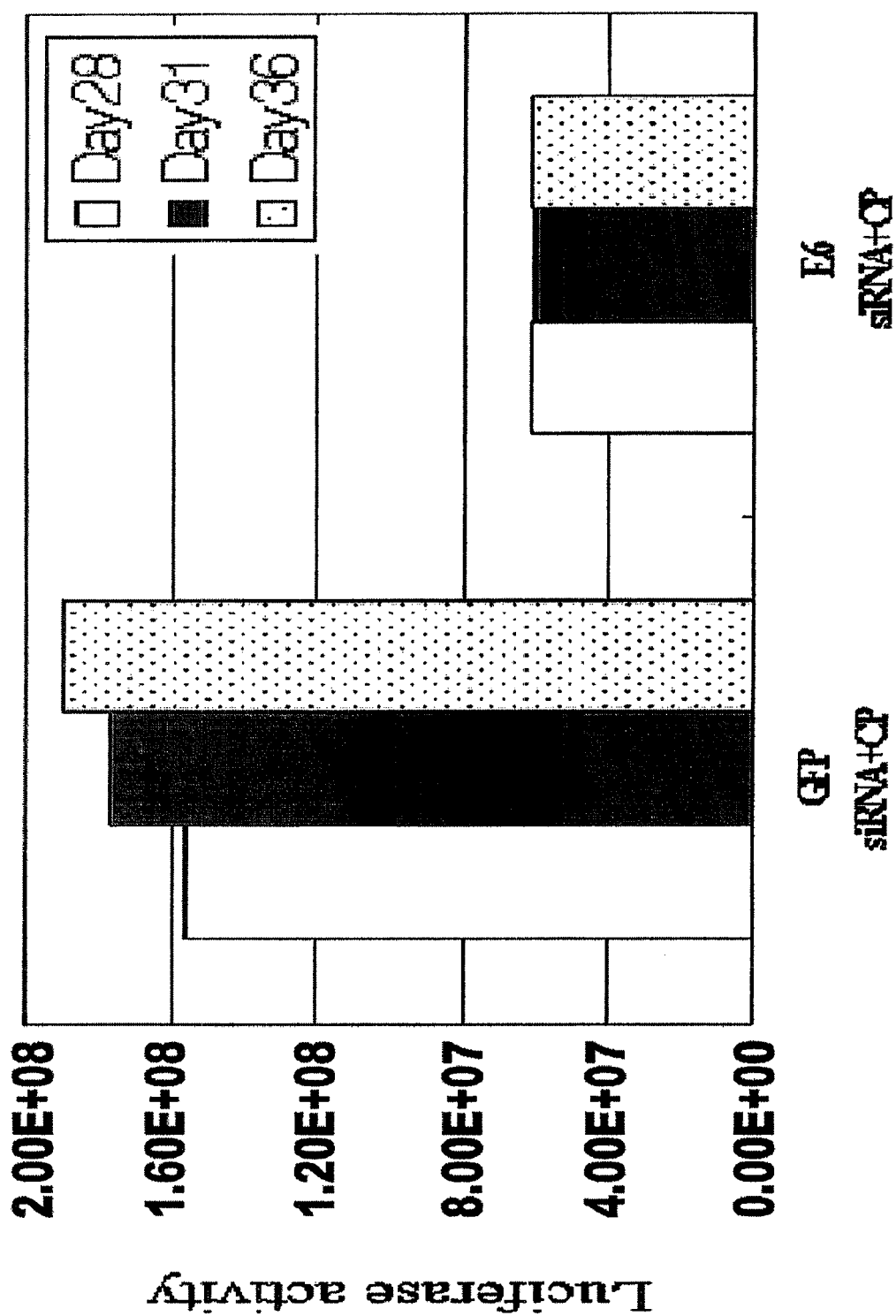

FIG. 23 is a graph illustrating the changes of the tumor size over the time in the animal xenograft model after combination therapy with GFP siRNA, E6 siRNA and cisplatin.

BEST MODE

Hereinafter, the present invention is described in detail.

The present invention provides a composition for the treatment of cancer comprising the first active part containing human papilloma virus (referred as "HPV" hereinafter) specific siRNA as an active ingredient and the second active part containing an anticancer agent at a low concentration as an active ingredient.

The first active part and the second active part can be premixed or independently administered stepwise. For the independent administration, the first active part is preferably treated at least twice at a regular interval and then the second active part is constantly treated.

The composition for the treatment of cancer of the present invention is composed of the first active part comprising HPV specific siRNA as an active ingredient and the second active part comprising an anticancer agent at a low concentration as an active ingredient. The siRNA of the first active part targets HPV E6 protein gene and is preferably selected from the sequences represented by SEQ. ID. NO: 1 and NO: 3-NO: 14, but not always limited thereto. In fact, any siRNA that has the sequence capable of silencing HPV E6 protein gene can be included in the composition for the treatment of cancer of the invention. The effective dose of HPV specific siRNA is 0.1-20 mg/kg, preferably 0.2-15 mg/kg and more preferably 0.4-10 mg/kg, but not always limited thereto.

The anticancer agent of the second active part can be selected from the group consisting of cisplatin, heptaplatin, carboplatin and riboplatin, but not always limited thereto and any anticancer agent well known to those in the art as a drug that can be prescribed for cervix cancer can be included in the composition for the treatment of cancer of the invention. The preferable concentration of the anticancer agent is less than 1.25 µM but not always limited thereto.

The HPV specific siRNA of the first active part and the anticancer agent of the second active part can be carried by liposome. And the liposome herein can be lipofectamine, oligofectamine, cationic lipid or lipid nanoparticles containing helper lipid for the purpose of enhancing intracellular delivery and having positive charge on their surfaces and 100-200 nm in particle size. Cationic polymers such as chitosan, polyethylenimine, polylysine and polyhistidine can also be used, but not always limited thereto and any liposome that is accepted in the drug delivery system well known to those in the art can be included in the composition for the treatment of cancer of the invention. The cancer herein is cervix cancer, head and neck cancer or any HPV related cancer.

The first active part and the second active part of the composition for the treatment of cancer of the present invention can be administered simultaneously. At this time, the first active part is administered at least twice at 12-48 hour intervals and then the second active part is administered for 7 days from the administration day 2.

The composition for the treatment of cancer of the present invention can be administered orally or parenterally, but parenteral administration is more preferred. The composition of the present invention can also include, in addition to the effective dose of the major components, the first active part and the second active part, one or more pharmaceutically acceptable carriers or additives for the administration. As a carrier, one or more ingredients selected from the group consisting of diluents, lubricants, binders, disintegrating agents, sweetening agents, stabilizers and preserving agents can be used. And as an additive, one or more ingredients selected from the group consisting of flavors, vitamins and antioxidants can be used. In this invention, any pharmaceutically acceptable carrier or additive can be used. Particularly, the diluent is preferably selected from the group consisting of lactose monohydrate, cornstarch, soybean oil, microcrystalline cellulose and D-mannitorl. The lubricant is preferably selected from the group consisting of magnesium stearate and talc. The binder is preferably selected from the group consisting of PVP (polyvinyipyrolidone) and HPC (hydroxypropylcellulose). The disintegrating agent is preferably selected from the group consisting of Ca—CMC (carboxymethylcellulose calcium), sodium starch glycolate, polacrylin potassium and cross-linked polyvinylpyrrolidone. The sweetening agent is preferably selected from the group consisting of white sugar, fructose, sorbitol and aspartame. The stabilizer is preferably selected from the group consisting of Ma-CMC (carboxymethylcellulose sodium), beta-cyclodextrin, white bee's wax and xanthan gum. The preserving agent is preferably selected from the group consisting of methyl p-hydroxy benzoate (methlparaben), propyl p-hydroxy benzoate (propylparaben) and potassium sorbate. The pharmaceutically acceptable additive is exemplified by emulsifying adjuvants, stabilizers, isotonic agents and pH regulators. Particularly, the additive can be selected from the group consisting of emulsifying adjuvants such as $C_6$-$C_{22}$ fatty acids (ex. caprylic acid, capric acid, lauric acid, myrstic acid, palmitic acid, stearic acid, oleic acid, linoleic acid, arachidonic acid and docosahexaenoic acid) or their pharmaceutically acceptable salts (ex. Sodium salt, potassium salt and calcium salt), albumin and dextran; stabilizers such as cholesterol and phosphatidic acid; isotonic agents such as sodium chloride, glucose, maltose, lactose, sucrose and trehalose; and pH regulators such as hydrochloric acid, sulfuric acid, phosphoric acid, acetic acid, sodium hydroxide and triethanolamine.

The composition for the treatment of cancer of the present invention can be formulated as liquids (injections, drops) prepared by dispersing the composition in aqueous solution or freeze-dried preparations thereof. In the case of liquid, the composition of the invention is preferably included at the concentration of 0.01-25% (w/v) and more preferably included at the concentration of 0.01-2% (w/v).

The composition for the treatment of cancer of the invention is preferably administered by unit dosage via intra-venous administration, intra-arterial administration, oral administration, intra-tissue administration, transdermal administration, mucosal administration or transrectal administration and particularly intra-venous administration, transdermal administration and mucosal administration are preferred. The preferable formulations for the administration are exemplified by injectable solutions, drops, absorbents, eye-drops, lotions and suppositories.

The present invention provides a method for preparing the composition for the treatment of cancer.

The present invention provides a method for preparing the composition for the treatment of cancer including the step of loading the HPV specific siRNA of the invention or an anti-cancer agent to the liposome. The loading is preferably performed by the conventional method well-known to those in the art.

The present invention further provides a method for treating cancer using the composition for the treatment of cancer of the invention.

The present invention provides a method for treating cancer comprising the following steps: 1) administering the effective dose of HPV specific siRNA to a patient once or twice for 24 hours; and 2) administering the effective dose of an anticancer agent at a low concentration to the patient for 4-7 days.

In this method, the effective dose of the HPV specific siRNA of step 1) is preferably 0.1-20 mg/kg, more preferably 0.2-15 mg/kg and most preferably 0.4-10 mg/kg, but not always limited thereto and can be determined by an experienced doctor with consideration of age and height of a patient, severity of disease, target area and excretion.

In this method, the effective dose of the anticancer agent of step 2) is preferably 0.1-250 μM, more preferably 0.5-200 μM and most preferably 0.625-160 μM, but not always limited thereto and can be determined by an experienced doctor with consideration of age and height of a patient, severity of disease, target area and excretion.

The present invention also provides a method for treating cancer comprising the following steps: 1) irradiating a patient; and 2) administering the effective dose of the anti-cancer agent at a low concentration to the patient for 4-7 days.

In this method, the irradiation amount of step 1) is preferably 0.1-30 Gy, more preferably 0.2-20 Gy and most preferably 0.3-16 Gy, but not always limited thereto and can be regulated by an experienced doctor with consideration of age and height of a patient, severity of disease, target area and excretion.

In this method, the effective dose of the anticancer agent of step 2) is preferably 0.1-250 μM, more preferably 0.5-200 μM and most preferably 0.625-160 μM, but not always limited thereto and can be regulated by an experienced doctor with consideration of age and height of a patient, severity of disease, target area and excretion.

The cancer herein is cervix cancer, head and neck cancer or any HPV related cancer.

The present inventors constructed HPV E6 or E7 specific siRNA (see Table 1 and FIG. 1) and then transfected the cervix cancer cell line HeLa (HPV18) with the siRNA to investigate the expression of p53 protein. As a result, the level of E6 protein was reduced in the HeLa cell line transfected with 18E6 siRNAs (18E6-1 and 18E6-2 siRNAs) but the level of p53 was increased. The changes of the levels of HPV18 E7 and pRb proteins were observed in the HeLa cell line transfected with 18E6-1 or 18E6-2 siRNA (see FIG. 2). The level of p53 was increased in the HeLa cell line treated with cisplatin, known as a conventional anticancer agent, over the time (see FIG. 3). HeLa cells were treated with different concentrations of cisplatin and cell survival rate was investigated. As a result, cell survival rate was decreased cisplatin dose-dependently (see FIG. 4).

Figure 5:
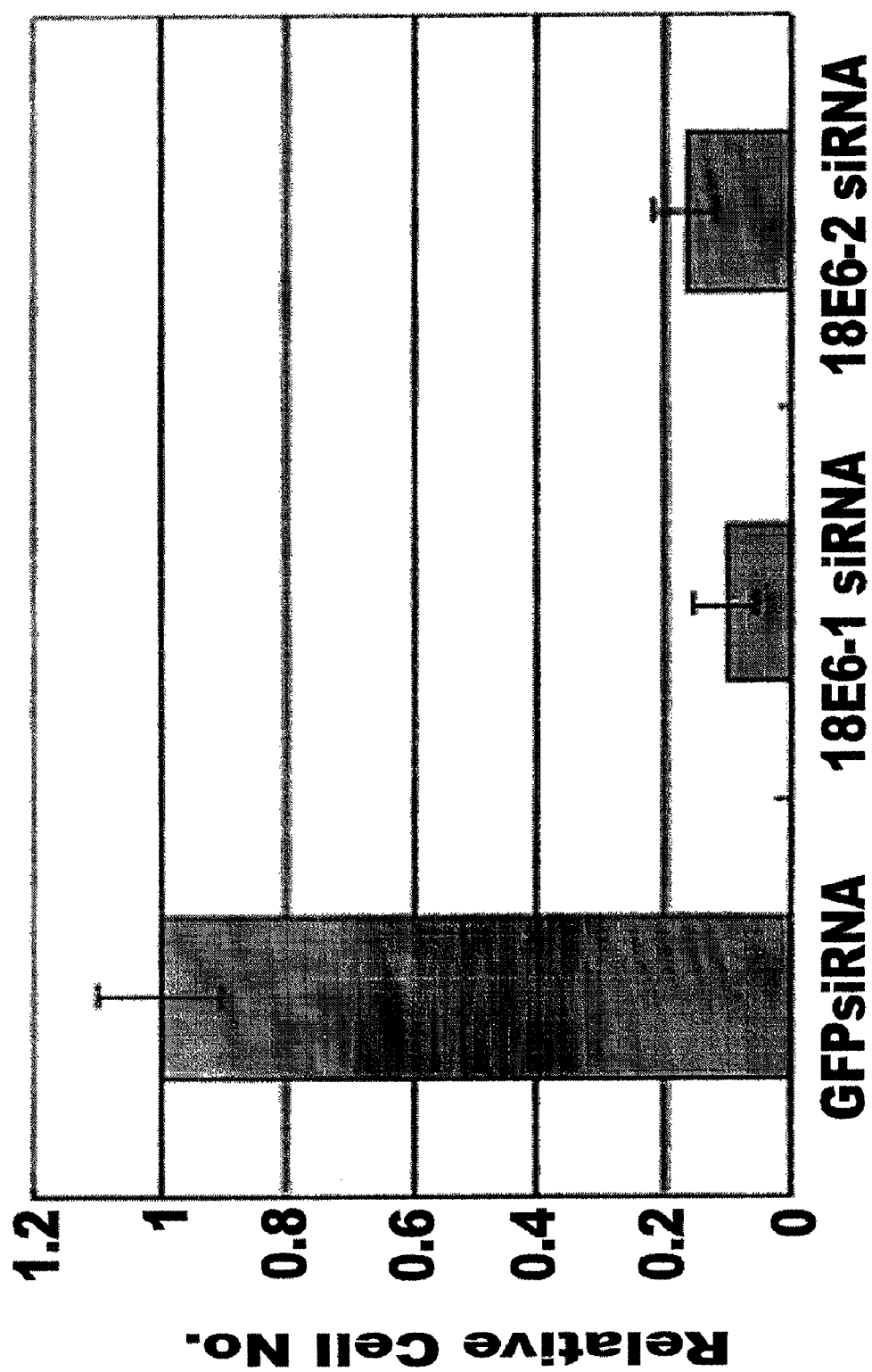
FIG. 5 illustrates the changes of cell number of HeLa cell line (HPV-18) after treating the cell line with pEBG vector as a control and GFP siRNA, 18E6-1 siRNA or 18E6-2 siRNA.
Figure 6:
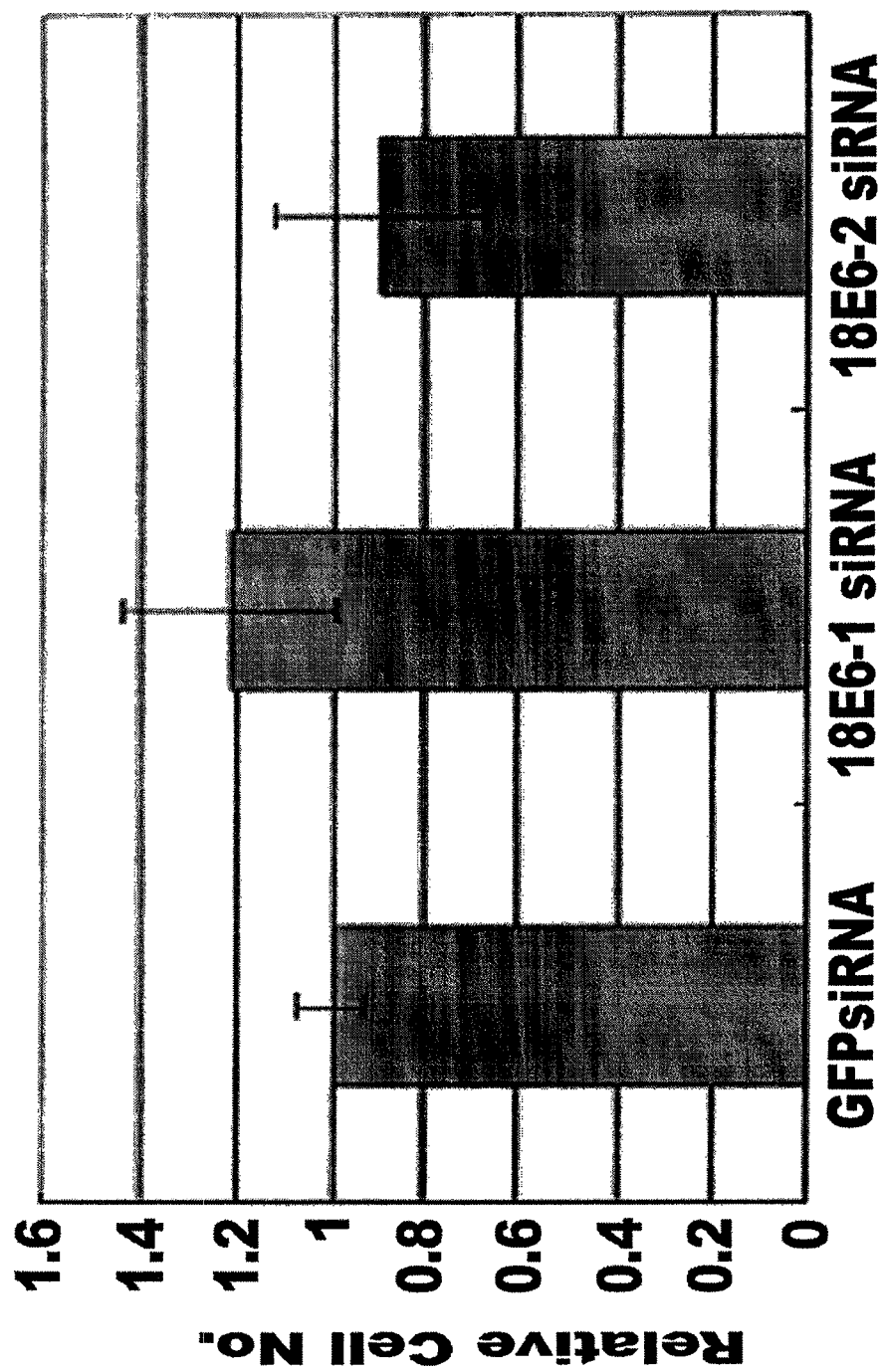
FIG. 6 illustrates the changes of cell number of HeLa cell line (HPV-18) after transfecting the cell line with HPV-16 E6 plasmid together with GFP siRNA, 18E6-1 siRNA or 18E6-2 siRNA.

The present inventors confirmed that the siRNA of the invention did not bring off-target effect (see FIGS. 5 and 6). The inventors further observed morphology of CaSki cell line (HPV-16) after transfection with 16E6 siRNA, 18E6-1 siRNA and 18E6-2 siRNA. As a result, no morphological change but normal cell growth was observed in the groups treated with GFP siRNA, 18E6-1 siRNA and 18E6-2 siRNA. On the other hand, cell number was decreased in the group treated with 16E siRNA (see FIG. 7). From the results, it was confirmed that the siRNA of the present invention is specifically involved in silencing of HPV E6 gene.

The present inventors confirmed the anticancer effect of the combination therapy of E6 siRNA and an anti-cancer agent. Particularly, the E6 siRNA of the invention was pre-administered and then cisplatin, the conventional anticancer agent, was administered over a long period of time at a low concentration (see FIG. 10a). As a result, the number of cells survived was not significantly decreased in the single therapy group, compared with the control, suggesting that the single therapy did not bring a satisfactory anticancer effect (see FIG. 10b). But, the number of cells survived in the combination therapy group was significantly reduced, compared with the control (see FIG. 10c). The cells of the single therapy group and the combination therapy group were cultured in normal media until 14 days, and then cell numbers were measured to judge cell recovery. As a result, the cell number was rapidly increased in the single therapy group, while the cell number was changed modestly in the combination therapy group (see FIG. 11). Media were replaced with normal media and cell numbers were measured on the $7^{th}$ and $14^{th}$ day of culture. The cell number of the single therapy group was 5-7 fold increased, while the cell number of the combination therapy group was approximately 3 fold increased (see FIG. 12). The above results indicate that cell recovery is slower in the combination therapy group than in the single therapy group.

The present inventors observed cell morphology both in the single therapy group and in the combination therapy group. As a result, in the single therapy group, cell growth was regular in the control and in the group treated with GFP siRNA or low concentration of cisplatin. On the contrary, cell growth was inhibited in the group treated with 18E6-1 siRNA or 18E6-2 siRNA, compared with the control and the group treated with GFP siRNA (see FIG. 13). In the combination therapy group, cell growth was inhibited by treating with cisplatin. In particular, cell growth of the group treated with 18E6 siRNA was significantly inhibited (see FIG. 13). Media were replaced with normal media and cell morphology was observed on the 7$^{th}$ day of culture. As a result, excessive cell growth was observed in the group treated with 18E6 siRNA alone, among the single therapy groups. Among the combination therapy groups, slower cell growth was observed in the group co-treated with 18E6 siRNA and low concentration of cisplatin (see FIG. 14).

The present inventors further investigated apoptosis and senescence in relation to the single therapy and the combination therapy. As a result, apoptosis was increased in the combination therapy group, compared with the single therapy group (see FIG. 15). And senescence was also increased in the combination therapy group, compared with the single therapy group (see FIGS. 16 and 17).

The present inventors compared the single radiotherapy and the combination therapy of radiotherapy and siRNA. As a result, cell density was lower in the group co-treated with radiotherapy and siRNA than in the group treated with radiotherapy alone (see FIG. 18).

The present inventors investigated whether the siRNA was successfully delivered to a target or not by using the conventional drug delivery system. As a result, successful siRNA delivery was confirmed (see FIGS. 19 and 20).

The present inventors also confirmed the anti-cancer effect of the E6 siRNA of the invention in the xenograft model. Particularly, the anticancer effect of the combination therapy of GFP siRNA or 18E-1 siRNA and cisplatin was greater than that of the group treated with GFP siRNA alone or 18E6-1 siRNA alone in a HeLa Luc cell line (see FIG. 21).

The present inventors investigated the changes of tumor size in the xenograft models each treated with GFP siRNA alone or E6 siRNA alone and co-treated with GFP siRNA or E6 siRNA and cisplatin. As a result, tumor size was reduced in the combination therapy group, compared with the group treated with GFP siRNA alone or E6 siRNA alone (see FIG. 22). The decrease of tumor size in the group co-treated with GFP siRNA and cisplatin was time-dependent, while the tumor size was not much changed in the group co-treated with E6 siRNA and cisplatin over the time (see FIG. 23).

The above results indicate that the composition for the treatment of cancer of the present invention is effective in treating cervix cancer and has advantage of reducing side effects generally induced by high concentration of an anti-cancer agent, specifically side effects shown in vivo experiment by the treatment of high concentration of cisplatin (5-10 mg/kg).

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Therapeutic Effect of E6 siRNA and Cisplatin on Cervix Cancer Cells

Figure 1:
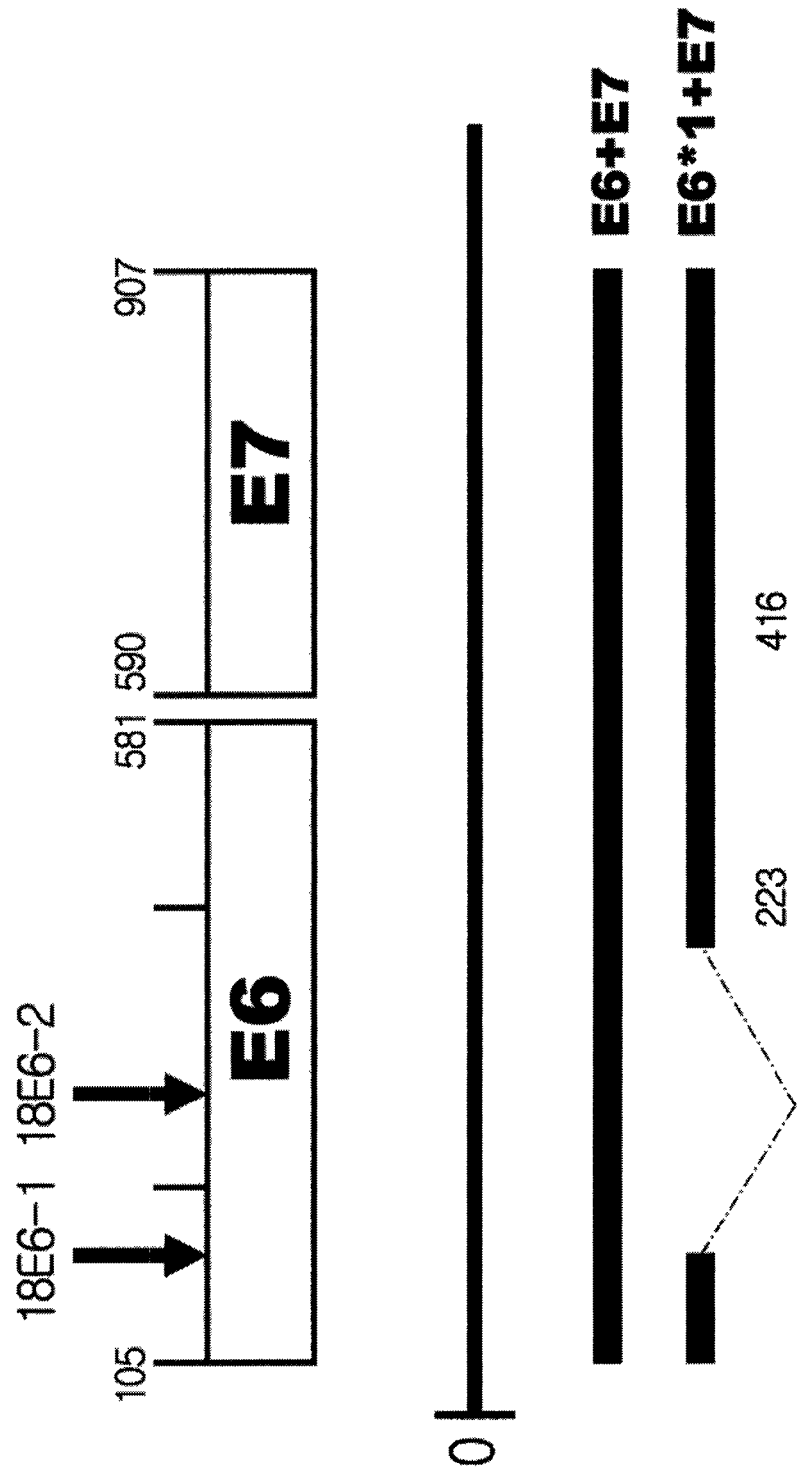
FIG. 1 is a schematic diagram illustrating the outlines of HPV (human papilloma virus) 18 E6 and E7 genes, in which the locations of siRNA targets, 18E6-1 and 18E6-2, on the nucleotide sequence, are indicated.

In the high risk HPV 18 type, E6 and E7 were transcribed as individual bicistronic pre-mRNA and 4 truncated forms of E6 (E6*I-VI mRNA) were generated by alternative splicing. Most of E7 protein were generated from the translation from E6*I mRNA. Thus, the present inventors asked Dharmacon Co. (USA) to synthesize siRNAs targeting different sequences of HPV 18 E6 mRNA and various HPV types (Table 1). 18E6-1 siRNA (targeting both full length E6 and E6*I mRNA) reduced levels of E6 and E7 mRNAs, while 18E6-2 siRNA only targeted full-length E6 mRNA. In the meantime, 16E6 siRNA targeted HPV-16 type E6 mRNA (FIG. 1). To investigate function of the synthetic siRNA, HeLa (HPV-18) cells were transfected with 18E6-1 siRNA or 18E6-2 siRNA. The cervix cancer cell line HeLa (HPV-18: KOREAN CELL LINE BANK, KCLB) was cultured in RPMI 1640 (Sigma Chemical Co.) supplemented with 10% FBS and antibiotics, at 37° C. with 5% $CO_2$ and 100% of humidity. 24 hours before the transfection, the cells were distributed in 100 mm plates ($1 \times 10^6$ cells/plate). Transfection was performed using oligofectamine (Invitrogen, USA) according to the instructions provided by Dharmacon Co. 24 hours after the transfection, Western blotting was performed to measure the level of p53. The cells were lysed by adding RIPA lysis buffer (150 mM NaCl, 10 mM Tris-HCl (pH 7.4), 5 mM EDTA, 0.1% SDS, 0.5% deoxycholate and 1% NP-40), followed by detection by Western blotting. Anti-p53 mouse antibody was purchased from Santa Cruz Co. (USA) and diluted at 1:1000. Goat-anti-mouse IgG HRP conjugate antibody was purchased from Jackson Laboratories Co. (USA) and diluted at 1:2000.

Figure 2:
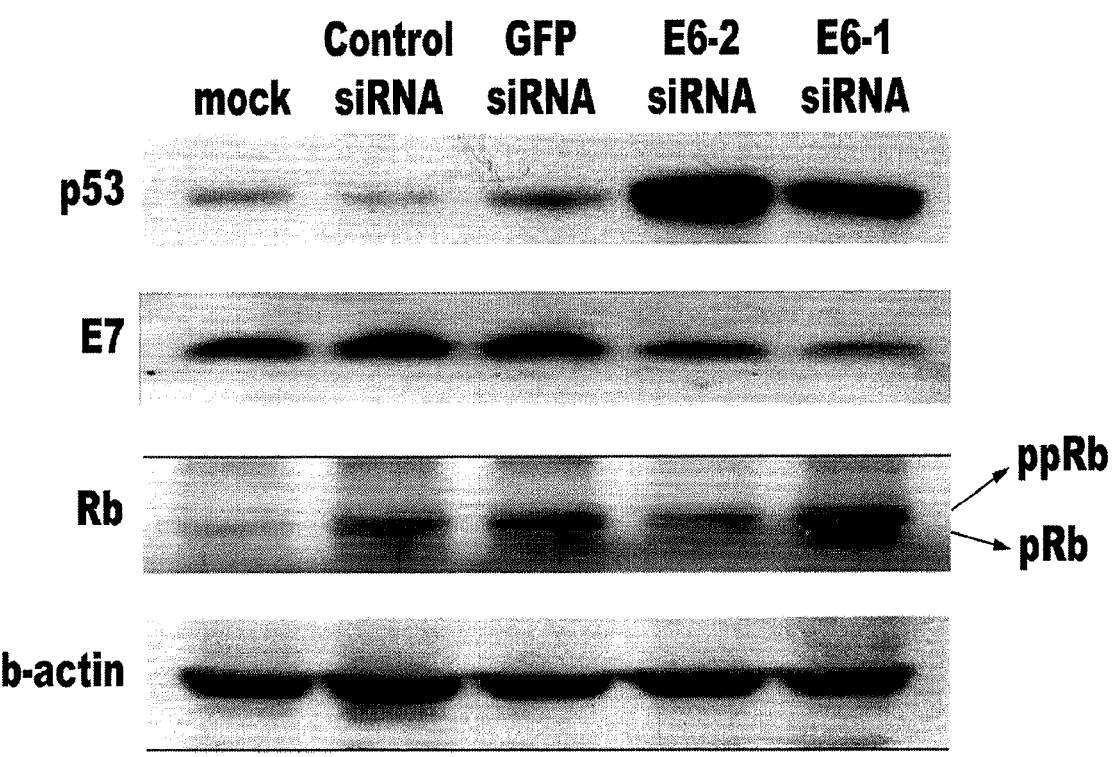
FIG. 2 illustrates the results of Western blotting examining the expressions of p53, E7 and Rb after the transfection of HeLa cells (HPV-18) with siRNA.

As a result, 18E6-1 and 18E6-2 siRNAs reduced the level of E6 protein and thus increased the level of p53 in HeLa cells. However, GFP siRNA and control siRNA did not change any protein level in HeLa cells (FIG. 2).

The changes of HPV18 E7 and pRb levels in association with 18E6 siRNAs (18E6-1 and 18E6-2 siRNAs) were also detected by Western blotting. Anti-HPV18 E7 goat antibody was purchased from Santa Cruz Co. and anti-pRb mouse antibody was purchased from BD Pharmingen Co. (USA). The level of E7 was reduced not by 18E6-2 siRNA but by 18E6-1 siRNA. Increase of the level of pRb hyperphosphorylated by 18E6-1 siRNA was observed (FIG. 2).

To investigate the effect of cisplatin on cervix cancer cells, HeLa cells were treated with cisplatin. 24 hours before the treatment, $1 \times 10^6$ cells were distributed in 100 mm culture dish and cultured at 37° C. with 5% $CO_2$ and 100% humidity. Then, the cells were treated with 40 μM of cisplatin. 24 hours later, Western blotting was performed to measure the level of p53.

Figure 3:
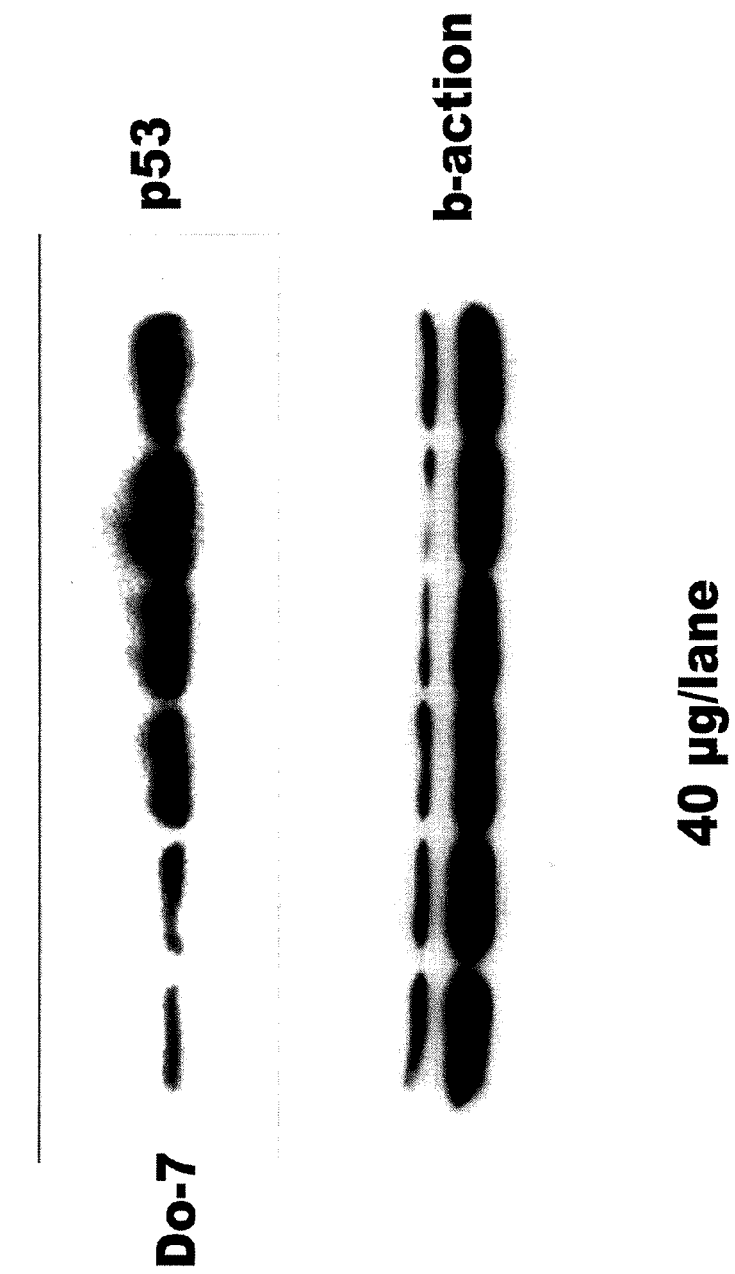
FIG. 3 illustrates the results of Western blotting analysis the expression of p53 over the time after the treatment of HeLa cells with cisplatin alone.

As a result, as shown in FIG. 3, the expression level of p53 was recovered and increased by chemotherapy with cisplatin. After treating 40 μM of cisplatin, the level of p53 was dramatically increased and 24 hours later the level reached the peak and then slowly reduced from then on, but the high level of p53 was constantly observed for 48 hours.

Figure 4:
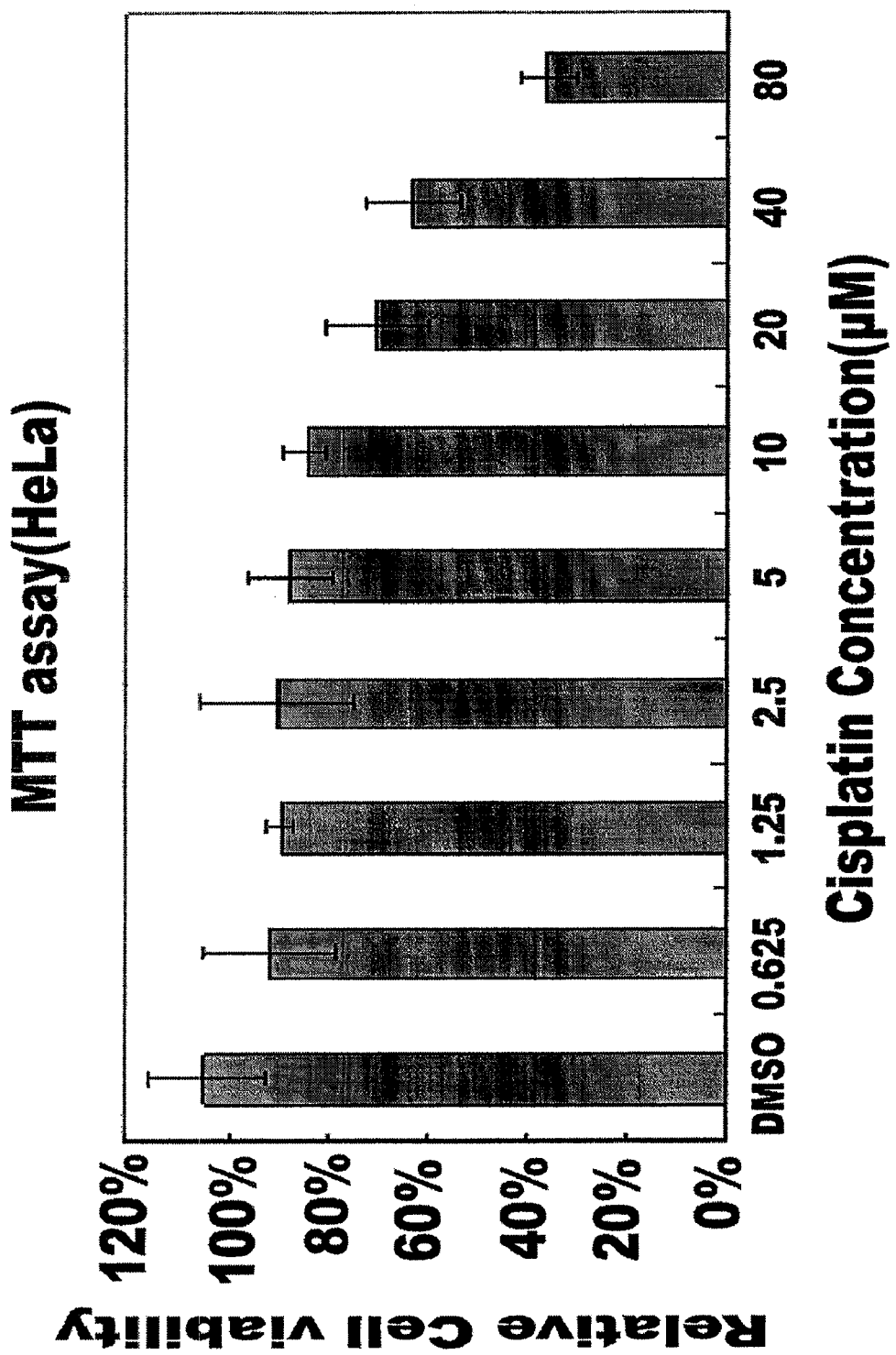
FIG. 4 illustrates the results of MTT assay examining the cell survival rates measured 24 hours after the single therapy of cisplatin at different concentrations.

The present inventors also investigated cytotoxic effect of cisplatin on HeLa cells by MTT assay. HeLa cells were treated with different concentrations of cisplatin (0.625, 1.25, 2.5, 5, 10, 25, 40, and 80 μM) for 48 hours, followed by MTT assay to measure the cell growth inhibitory effect. As a result, cell survival rate of the cervix cancer cells was reduced cisplatin dose dependently (FIG. 4).

TABLE 1

| siRNA | Target sequence | Target transcript | SEQ. ID. NO. |
|---|---|---|---|
| 18E6-1 | 5'-TAACCTGTGTATATTGCAA-3' | E6*mRNA, full length E6 mRNA | 1 |
| 18E6-2 | 5'-CTAACTAACACTGGGTTAT-3' | full length E6 mRNA | 2 |
| 16E6-1 | 5'-ACCGTTGTGTGATTTGTTA-3' | | 3 |

TABLE 1-continued

| siRNA | Target sequence | Target transcript | SEQ. ID. NO. |
|---|---|---|---|
| 16E6-2 | 5'-AAAGAGAACTGCAATGTTT-3' | | 4 |
| 31E6 | 5'-AAAGGTCAGTTAACAGAAA-3' | | 5 |
| 33E6 | 5'-AACGACATGTGGATTTAAA-3' | | 6 |
| 35E6 | 5'-CCAGCTGAACGACCTTACA-3' | | 7 |
| 45E6 | 5'-ATATGCTGCATGCCATAAA-3' | | 8 |
| 52E6-1 | 5'-GAAGAGAGGTATACAAGTT-3' | | 9 |
| 52E6-2 | 5'-CAAACAAGCGATTTCATAA-3' | | 10 |
| 56E6-1 | 5'-TAACACGTGCTGAGGTATA-3' | | 11 |
| 56E6-2 | 5'-AGATGTCAAAGTCCGTTAA-3' | | 12 |
| 58E6-1 | 5'-CCACGGACATTGCATGATT-3' | | 13 |
| 58E6-2 | 5'-TGCTTACGATTGCTATCTAAA-3' | | 14 |
| GFP | 5'-GGCTACGTCCAGGAGCGCACC-3' | | 15 |

EXAMPLE 2

Effect of HPV18 E6 siRNA without "Off-target Effect"

After confirming that the 18E6 siRNA was a target specific, the present inventors constructed HPV16-E6 plasmid. HeLa cells were transfected with the plasmid together with 18E6-1 siRNA or 18E6-2 siRNA. The HPV16-E6 plasmid was cloned in between BamHI and NotI sites of pEBG vector by inserting HPV16 E6 gene (KW Jeong et al, Oncogene 1-13, 2006).

In the control group, the treatment of 18E6-1 siRNA and 18E6-2 siRNA also reduced the cell number, which was consistent with the above results (FIG. 5). However, the cell number in the group transfected with HPV16 E6 plasmid did not decrease with the treatment of 18E6 siRNA because of the expression of HPV16 E6 (FIG. 6).

The present inventors further observed morphology of the cells under phase-contrast microscope (AxioVision, Carl Zeiss, German) after transfecting HPV-16 CaSki cells with 16E6 siRNA, 18E6-1 siRNA or 18E6-2 siRNA.

Figure 7:
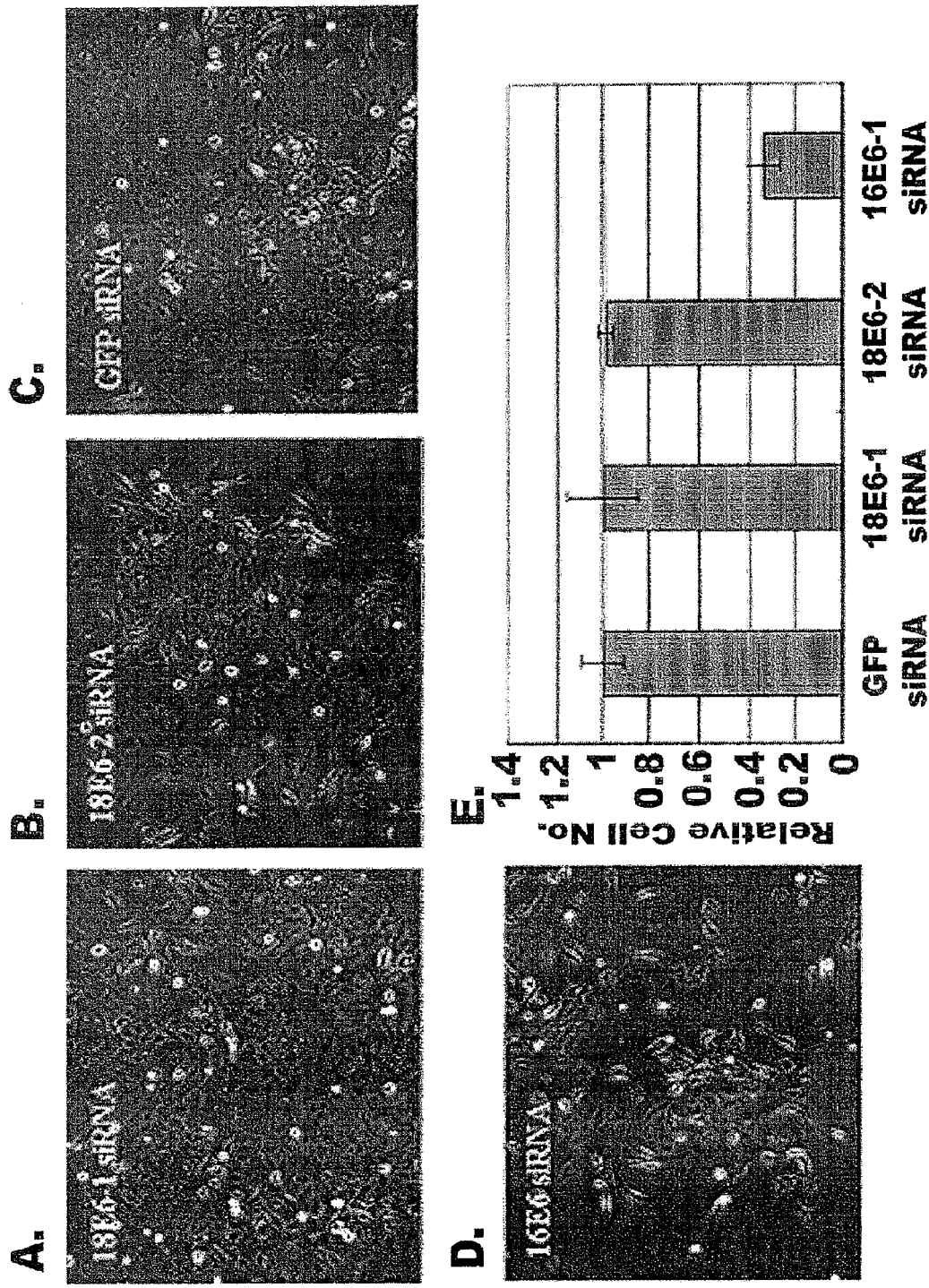
FIG. 7 is a diagram illustrating the cell number and morphology of CaSki cells (HPV-16) after treating the cells with 16E6 siRNA, 18E6-1 siRNA and 18E6-2 siRNA:
  A: 18E6-1 siRNA;
  B: 18E6-2 siRNA;
  C: GFP siRNA;
  D: 16E6 siRNA; and
  E: cell number counting graph.

As a result, the cell growth was observed in the group treated with 18E6-1 siRNA and 18E6-2 siRNA as in the group treated with GFP siRNA, but no morphological changes were observed. In the meantime, the cell number of the group treated with 16E6 siRNA was reduced (FIG. 7).

From the results, it was confirmed that the 18E6-1 siRNA or 18E6-2 siRNA of the present invention specifically induced gene silencing without off-target effect.

EXAMPLE 3

Cytotoxic Effect of the Short Term Combination Therapy of E6 siRNA and Cisplatin The present inventors investigated cytotoxic effect of the combination therapy of E6 siRNA and cisplatin chemotherapy on cervix cancer cells. HPV-18 HeLa cells ($1\times10^4$ cells/well) were treated with GFP and 100 nM of 18E6-1 siRNA or 18E6-2 siRNA targeting HPV18 E6, followed by culture in a 96-well plate for 12, 24 and 48 hours. The cells transfected with 18E6-2 siRNA were treated with different concentrations of cisplatin (5, 10, 20, 40, 80 and 160 µM) for 0, 24 and 48 hours. Cell survival rate was measured by MTT assay.

Figure 8:
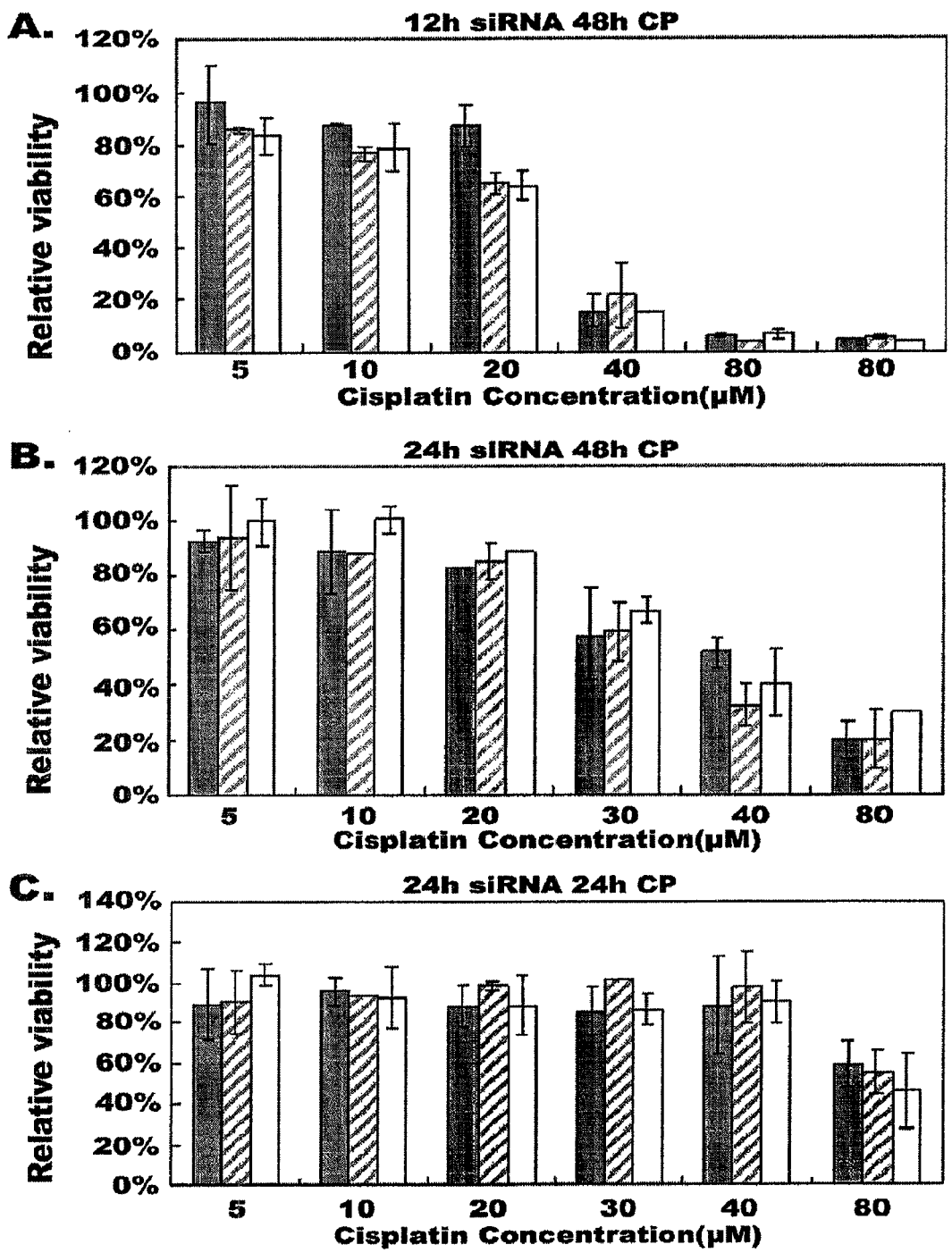
FIG. 8 is a graph illustrating the cell survival rate of HeLa cells co-treated with 18E6-2 siRNA and cisplatin for a short term, measured by MTT assay:
  A: HeLa cells treated with siRNA for 12 hours and then treated with cisplatin for 48 hours;
  B: HeLa cells treated with siRNA for 24 hours and then treated with cisplatin for 48 hours; and
  C: HeLa cells treated with siRNA for 24 hours and then treated with cisplatin for 24 hours.

As a result, as shown in FIG. 8, cell survival rate was not much different between the group treated with cisplatin alone (black rod) and the group co-treated with 18E6-2 siRNA (white rod) or GFP siRNA (striped rod) and cisplatin.

The present inventors investigated cytotoxic effect of the combination therapy of 16E6 siRNA and cisplatin chemotherapy on HPV-16 cervix cancer cells. HPV-16 SiHa cells and CaSki (ATCC CRL1550) cells ($1\times10^4$ cells/well) were transfected with 100 nM of siRNA targeting HPV-16 E6 or GFP, followed by culture in a 96-well plate for 24 hours. 24 hours later, the cells transfected with siRNA were treated with different concentrations of cisplatin (5, 10, 20, 40 and 80 µM) for 24 hours. Cell survival rate was measured by MTT assay.

Figure 9:
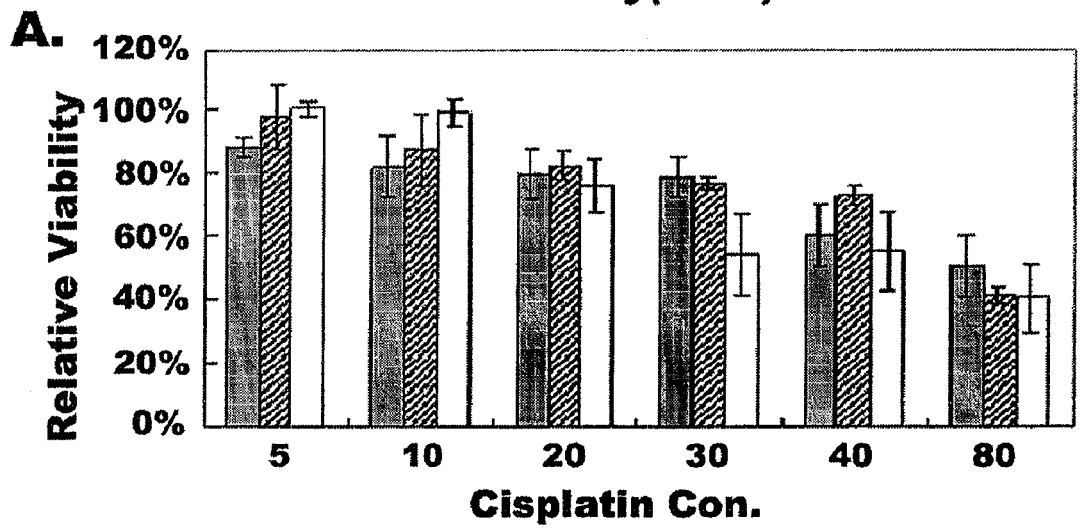
FIG. 9 is a graph illustrating the cell survival rates of SiHa cells or CaSki cells analyzed by MTT assay after short-term combination therapy of 18E6-2 siRNA and cisplatin:
  A: SiHa cells; and
  B: CaSki cells.
Figure 9:
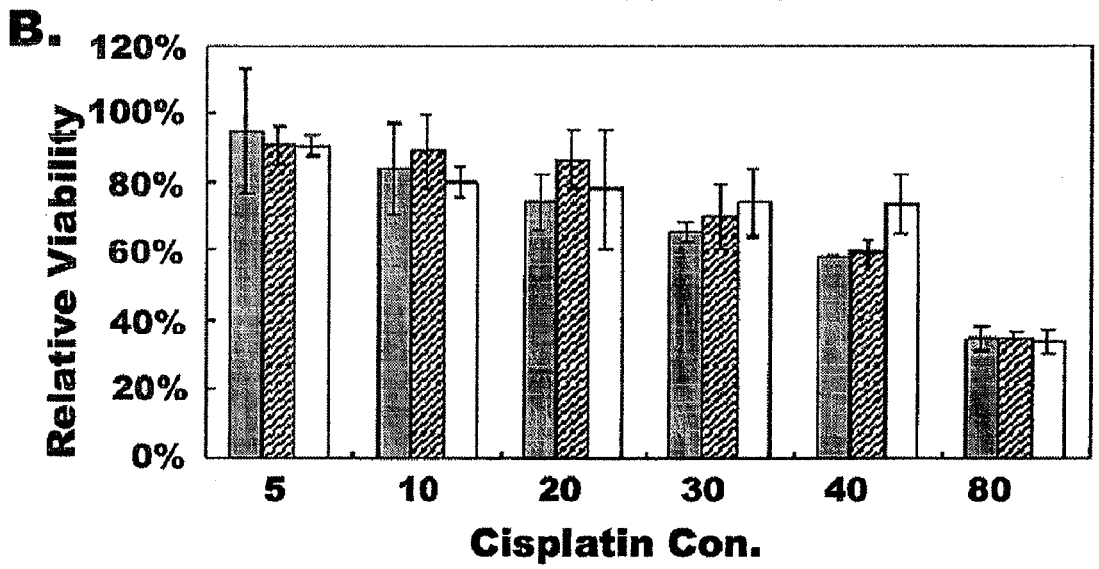

As shown in FIG. 9, cell survival rate was not much different between the group treated with cisplatin alone and the group co-treated with cisplatin and 16E6 siRNA or GFP siRNA.

The above results indicate that there is no synergy effect on cytotoxicity by the short-term combination therapy of E6 siRNA and cisplatin in cervix cancer cells.

EXAMPLE 4

Cytotoxic Effect of the Long-Term Combination Therapy of E6 siRNA and Cisplatin

To evaluate cytotoxic effect of the long-term combination therapy of synthetic E6 siRNA and cisplatin chemotherapy on cervix cancer cells, HeLa cells were co-treated for a long period of time.

Figure 10:
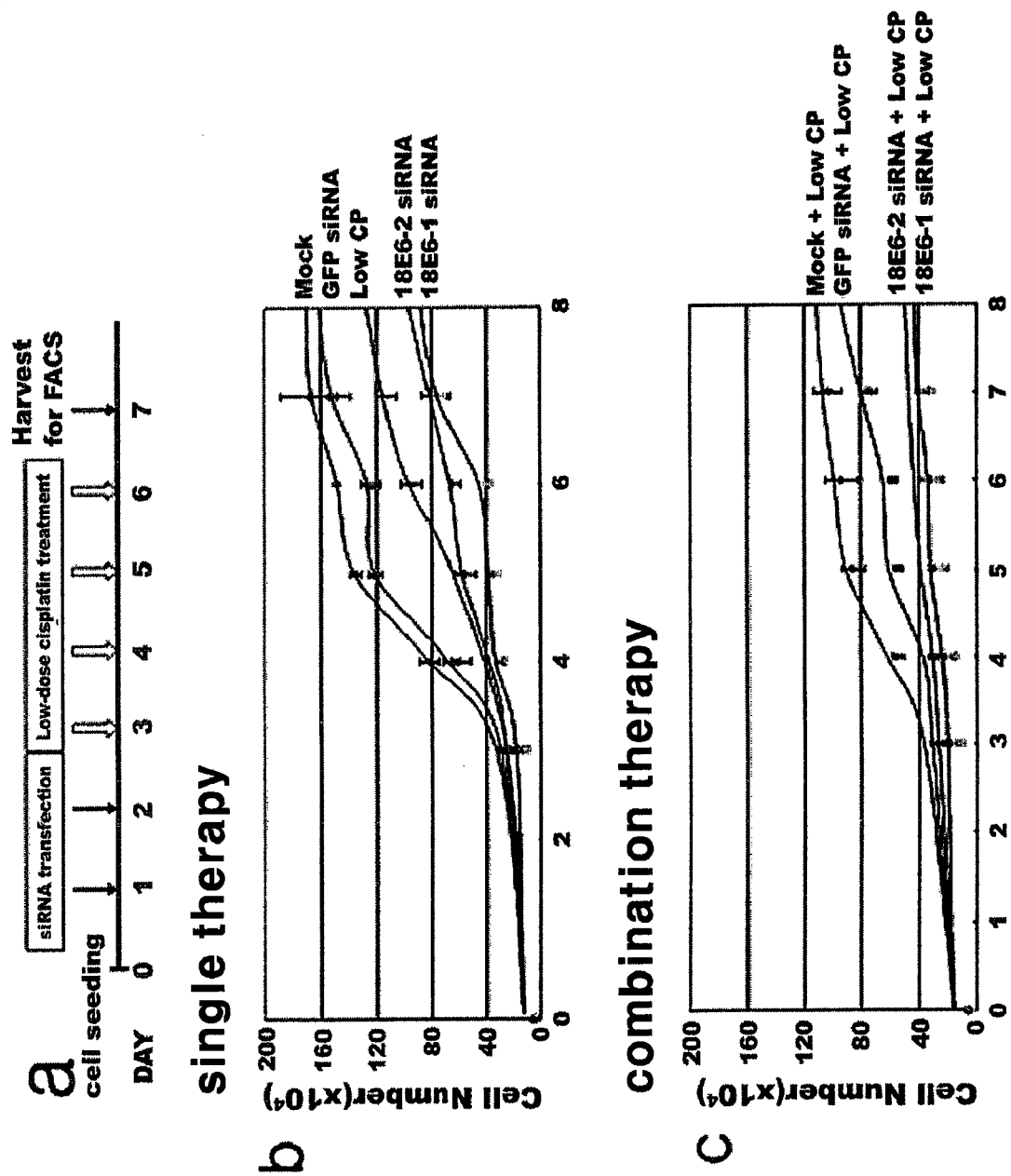
FIG. 10 illustrates the results of single therapy and combination therapy:
  a: schematic diagram illustrating long-term combination therapy;
  b: cell number of the group with single therapy; and
  c: cell number of the group with combination therapy.

Then, the single therapy group (treated with 18E6-1 siRNA, 18E6-2 siRNA or cisplatin alone) and the combination therapy group (treated with cisplatin and 18E6-1 siRNA or 18E6-2 siRNA) were compared. To obtain the maximum RNAi efficiency, siRNA transfection was repeated after 24 hours from the first transfection. For the transfection, 13 µl of opti-MEM (Gibco, USA) and 2 µl of oligofectamine were added into a 1.5 ml E-tube. To the other 1.5 ml E-tube were added 100 nM of siRNA and opti-MEM to make total volume 85 µl. 5 minutes later, the content of the E-tube containing oligofectamine was transferred into the other E-tube to make the total volume 200 µl, which stood by for 20 minutes to form a complex. In the meantime, the 6-well plate pre-inoculated with HeLa cells ($5\times10^4$ cells/well) 24 hours ago was washed once with PBS, to which 800 µl of serum free RPMI1640 was added. 20 minutes later, 200 µl of siRNA-oligofectamine complex was added into each well, followed by culture at 37° C. with 5% $CO_2$ and 100% humidity for 4 hours. 4 hours later, 500 µl of RPMI1640 containing 30% FBS was added thereto, followed by transfection. The combination therapy group was treated with a low concentration of cisplatin (1.25 µM) for 4 days after two time siRNA transfection (FIG. 10a). On the $7^{th}$ day of culture, the cells were recovered by treating with trypsin, stained with 0.3% trypan blue solution and counted with hemocytometer.

As a result, as shown in FIG. 10b, cell growth was significantly inhibited in the single therapy group treated with 18E6-1 siRNA or 18E6-2 siRNA alone. In particular, cell growth inhibitory effect was more significant in the group treated with 18E6-2 siRNA. In the meantime, cell growth inhibitory effect was not significant in the group treated with cisplatin alone.

As shown in FIG. 10c, cell growth was 2-3 fold reduced in the combination therapy group, compared with the single therapy group. Cell growth was significantly inhibited in the group co-treated with cisplatin and 18E6-1 siRNA or 18E6-2 siRNA.

The above results indicate that the long-term combination therapy of cisplatin and synthetic 18E6-1 siRNA or 18E6-2 siRNA in HeLa cells brings cytotoxic effect dramatically, compared with the single therapy.

Figure 11:
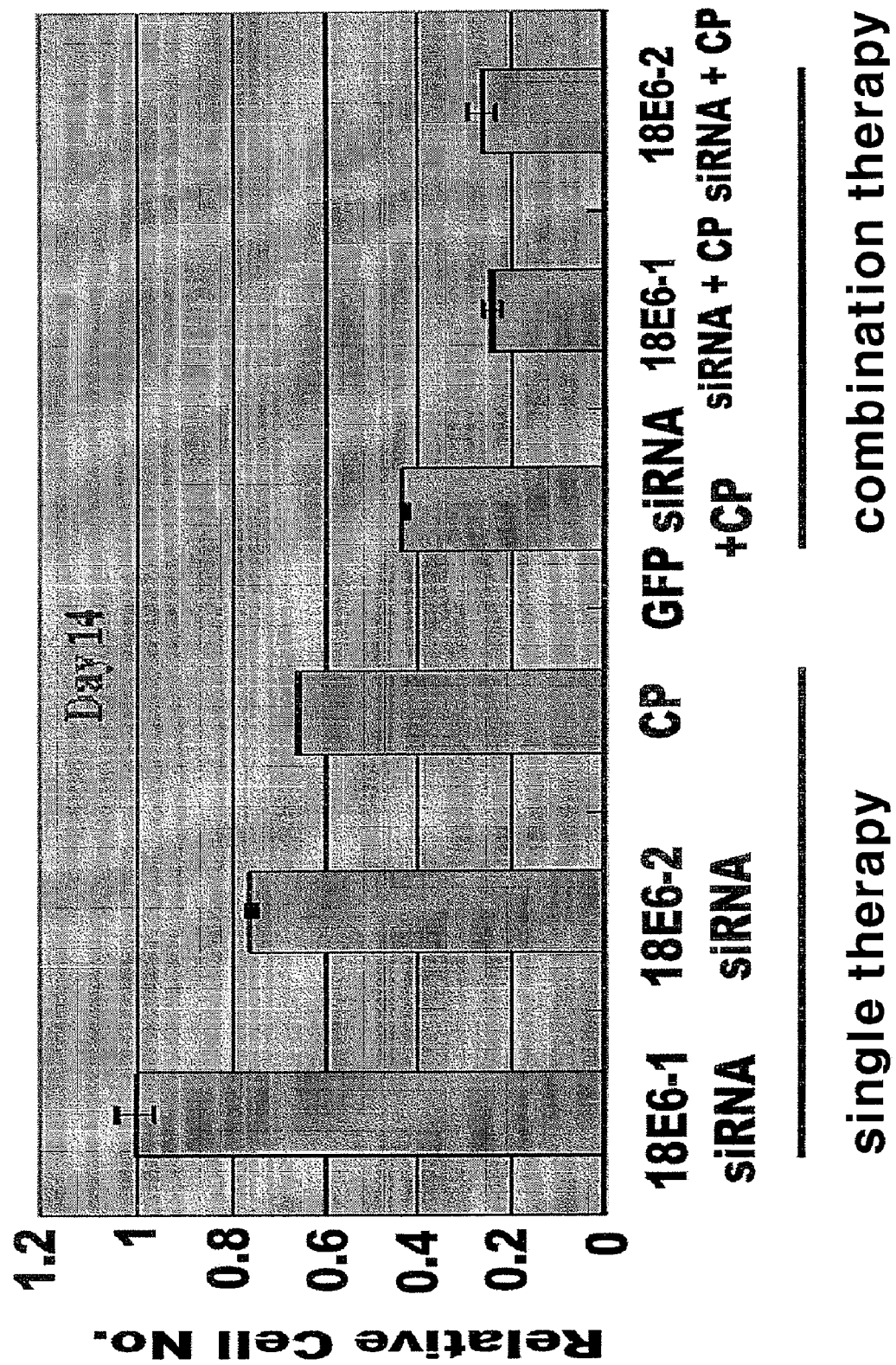
FIG. 11 is a graph illustrating the cell numbers of the group with single therapy and the group with combination therapy which were counted on the $14^{th}$ day of culture in normal media.

The cells were cultured in normal growth medium for additional 7 days, and harvested by treating them with trypsin. The cells were stained with 0.3% trypan blue and counted with hemocytometer (FIG. 11). Among the single therapy groups, the group treated with 18E6-1 siRNA exhibited the rapid cell growth. However, the cells of the groups treated with mock or GFP siRNA were over-grown. On the $14^{th}$ day in the combination therapy groups, the number of cells of the group treated with 18E6-1 siRNA or 18E6-2 siRNA was comparatively small or not increased.

Figure 12:
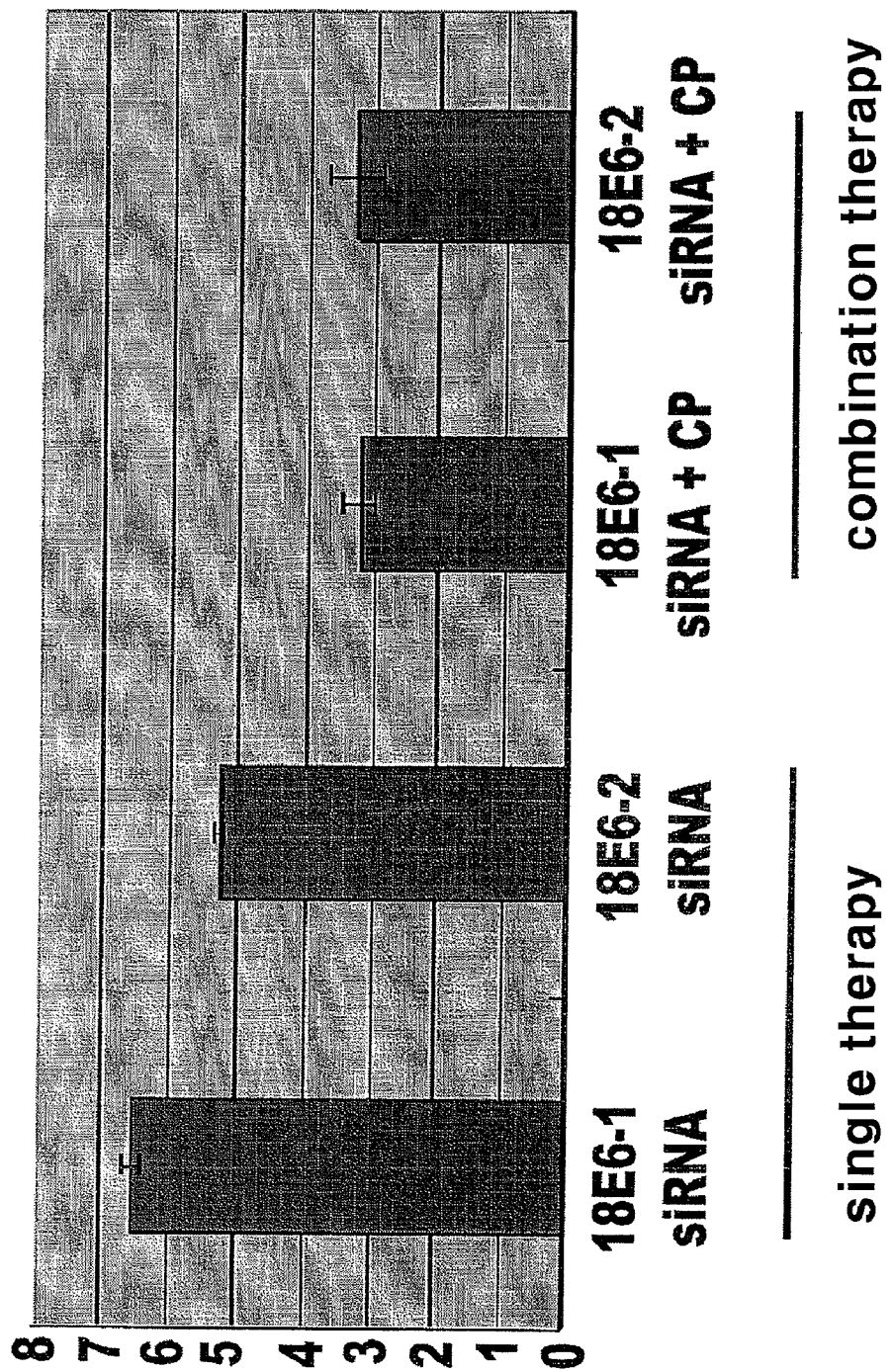
FIG. 12 is a graph illustrating the relative increasing rates of cell density of the group with single therapy and the group with combination therapy, which were compared on the $7^{th}$ and the $14^{th}$ day of culture in normal media.

As shown in FIG. 12, the cell numbers were standardized on the $7^{th}$ day according to the cell number of the group treated with 18E6-1 siRNA alone. For a week after day 7, the cell number of the single therapy group treated with 18E6-1 siRNA or 18E6-2 siRNA was 5-7 fold increased, while the cell number of the combination therapy group was approximately 3 fold increased.

In the combination therapy group, the cell recovery of the group co-treated with cisplatin and 18E6-1 siRNA or 18E6-2 siRNA was rather slow than the single therapy group each treated with 18E6-1 siRNA alone or 18E6-2 siRNA alone.

EXAMPLE 5

Effect of the Combination Therapy of Cisplatin and E6 siRNA on Cell Morphology

Figure 13:
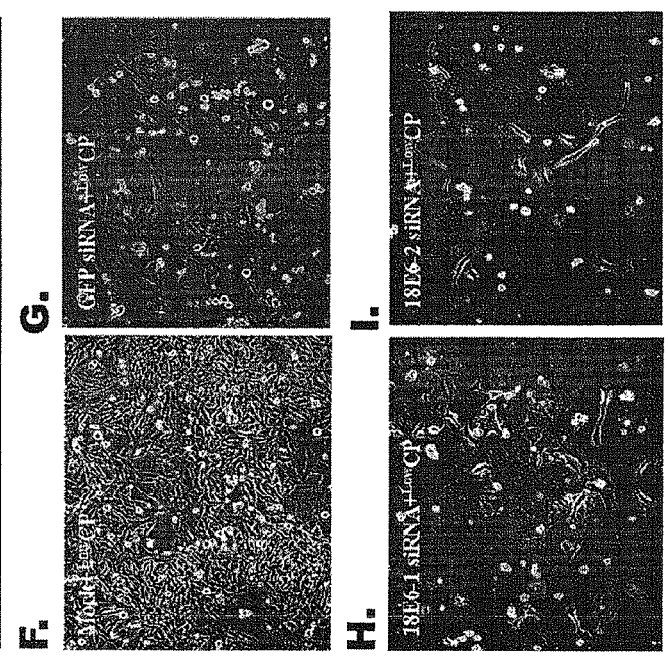
FIG. 13 is a photograph illustrating the morphology of the cells of the group with single therapy and the group with combination therapy on the $7^{th}$ day of culture:
  A: Mock;
  B: GFP siRNA;
  C: 18E6-1 siRNA;
  D: 18E6-2 siRNA;
  E: low Cisplatin;
  F: Mock+low Cisplatin;
  G: GFP siRNA+low Cisplatin;
  H: 18E6-1 siRNA+low Cisplatin; and
  I: 18E6-2 siRNA+low Cisplatin.
Figure 13:
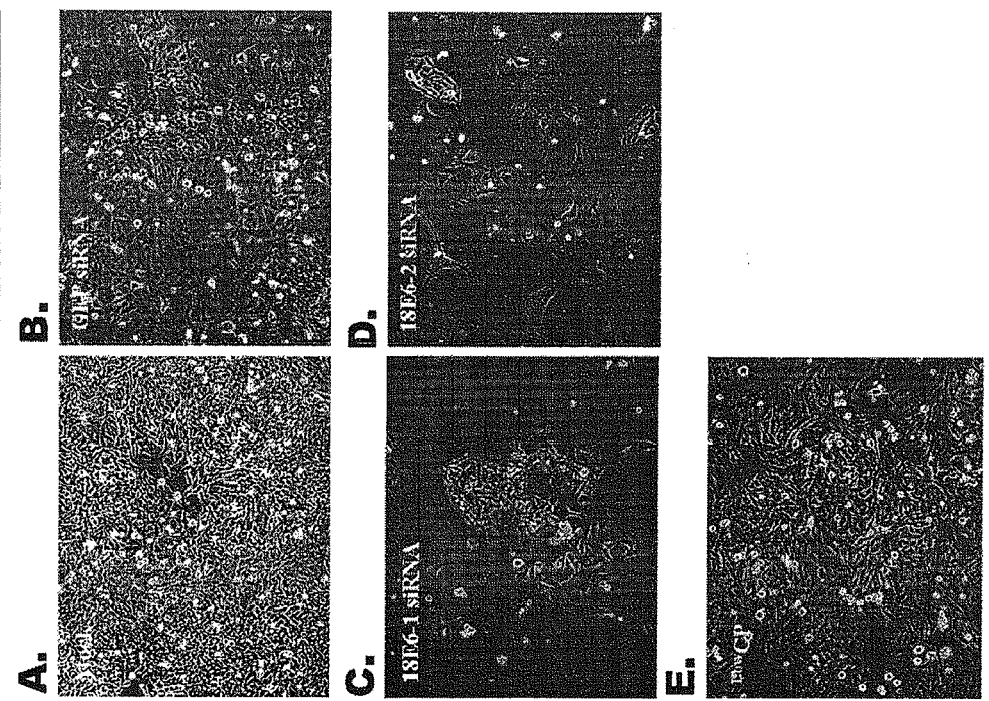

The present inventors observed morphology of the cells of the single therapy group and the combination therapy group on the $7^{th}$ day of the treatment under phase contrast microscope (AxioVision, Carl Zeiss, Germany). The cells of the group treated with mock, GFP siRNA or cisplatin alone were grown regularly. The cells of the group treated with 18E6-1 siRNA or 18E6-2 siRNA were not growing but from the $7^{th}$ day of the treatment small colonies which began to grow were observed. Morphological changes were observed in the cells treated with 18E6-1 siRNA and with 18E6-2 siRNA. Particularly, the cells treated with 18E6-1 siRNA were flat, round and enlarged. The cells treated with 18E6-2 siRNA were flatter and more enlarged (FIG. 13). On the contrary, the cell growth of the combination therapy group was inhibited by the treatment of cisplatin and the cell growth inhibitory effect was more significant in the cells treated with 18E6 siRNA together. Most of the cells co-treated with cisplatin and 18E6-1 siRNA or 18E6-2 siRNA were much flatter or thinner to death, compared with the cells of the single therapy group (FIG. 13).

Figure 14:
FIG. 14 is a photograph illustrating the morphology of the cells on the $14^{th}$ day of culture in normal media after single therapy and combination therapy.
Figure 14:
Figure 14:
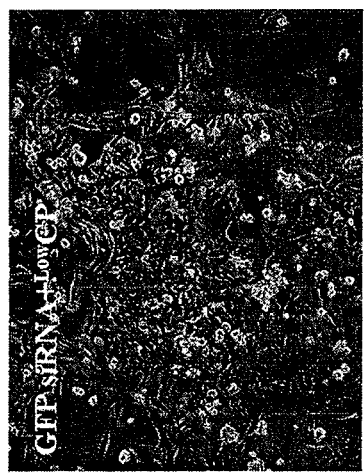
Figure 14:
Figure 14:

The present inventors cultured the cells in normal media additionally for 7 days to observe morphological changes. In the single therapy group treated with 18E6-1 siRNA or 18E6-2 siRNA, survived cells were proliferated excessively and particularly the group treated with 18E6-1 siRNA exhibited the fastest cell recovery (FIG. 14). In the combination therapy groups, cell growth of the group treated with GFP siRNA was significant but cell recovery of the group treated with 18E6-1 siRNA or 18E6-2 siRNA was very slow (FIG. 14).

EXAMPLE 6

Effect of the Combination Therapy of Cisplatin and 18E6 siRNA on Apoptosis and Senescence To examine apoptosis in the cells treated with 18E6-1 siRNA or 18E6-2 siRNA, the cells attached on the $7^{th}$ day of the treatment were collected, stained with annexin V and propidium iodide (PI) and analyzed by flow cytometry. Apoptosis rates between the single therapy group and the combination therapy group were compared.

As shown in FIG. 15, apoptosis was increased in HeLa cells treated with 18E6-1 siRNA or 18E6-2 siRNA. However, apoptosis was not increased in the single therapy group treated with GFP siRNA or cisplatin. Apoptosis of the combination therapy group was more increased than the single therapy group. Apoptosis was significantly increased in the cells co-treated with cisplatin (even at a low concentration) and 18E6-1 siRNA or 18E6-2 siRNA.

The above results indicate that 18E6-1 siRNA or 18E6-siRNA induced apoptosis in HPV18 related cancer cells. The apoptotic effect was greater when cisplatin was co-treated with 18E6 siRNAs.

The present inventors further investigated whether the combination therapy of cisplatin with 18E6 siRNAs induced HeLa cell senescence. The inventors measured SA β-Gal activity on the $7^{th}$ day of the treatment. The cells were washed with PBS using a senescence detection kit (BIoVision, USA) and treated with SA-β-gal staining solution at 37° C. for 12 hours. The cells stained with blue were observed under microscope (×100-200).

As a result, the stained cells were not detected in the single therapy group treated with mock or control siRNA, while some of the blue cells, a marker of senescence, were detected in the group co-treated with 18E6-1 siRNA or 18E6-siRNA and cisplatin at a low concentration. In the meantime, almost every cells of the combination therapy group treated with cisplatin and 18E6-1 siRNA or 18E6-2 SiRNA were stained dark blue, indicating a strong SA-β-Gal activity (FIG. 16).

Three photographs of the cells were taken randomly to investigate the stained cells (FIG. 17). Only a small number of cells were stained in the single therapy group treated with 18E6-2 siRNA, while a large number of cells were stained in the single therapy group treated with 18E6-1 siRNA. Only a small amount of cells were stained in the single therapy group treated with cisplatin at a low concentration. However, most of the cells were stained in the combination therapy group treated with 18E6-1 siRNA and cisplatin.

The above results indicate that the treatment of cisplatin at a low concentration significantly enhances the effect of 18E6-1 siRNA on senescence.

EXAMPLE 7

Cytotoxic Effect of the Combination Therapy of E6 siRNA and Radiotherapy

The present inventors examined cytotoxic effect of the combination therapy of synthetic E6 siRNA and radiotherapy on cervix cancer cells. Particularly, HeLa cells were irradiated with a low level (2 Gy). 24 hours later, the cells were treated with 18E6-1 siRNA or 18E6-2 siRNA twice and then cell number was measured on the $7^{th}$ day of the treatment.

As a result, cell number of the combination therapy group treated with 18E6-1 siRNA or 18E6-2 siRNA was smaller than that of the single therapy group treated with radiotherapy alone (FIG. 18).

The above results indicate that cytotoxic effect in HeLa cells was increased by the combination therapy of synthetic 18E6-1 siRNA or 18E6-2 siRNA with radiotherapy, compared with the single therapy of radiotherapy.

EXAMPLE 8 siRNA Delivery

The present inventors investigated whether the siRNA could be successfully delivered into a target cell or not, using oligofectamine (Invitrogen, USA). 13 μl of opti-MEM (Gibco, USA) and 2 μl of oligofectamine were added into a 1.5 ml E-tube. 100 nM of siRNA and opti-MEM were added into another 1.5 ml E-tube to make total volume 85 μl. 5 minutes later, the content of the E-tube containing oligofectamine was transferred into the other E-tube to make the total volume 200 μl which stood by for 20 minutes to form a complex. In the meantime, the 6-well plate pre-inoculated with HeLa cells ($5\times10^4$ cells/well) 24 hours ago was washed once with PBS, to which 800 μl of serum free RPMI1640 was added. 20 minutes later, 200 μl of siRNA-oligofectamine complex was added into each well, followed by culture at 37° C. with 5% $CO_2$ and 100% humidity for 4 hours. 4 hours later, 500 μl of RPMI1640 containing 30% FBS was added thereto, followed by transfection. siRNA was treated thereto twice by the same manner as described above and the cell number and morphology were investigated on the $6^{th}$ day of transfection. The cells were recovered by treating with trypsin, stained with 0.3% trypan blue solution and counted with hemocytometer.

As a result, as shown in FIGS. 19 and 20, the cells of the group treated with mock or GFP siRNA were not much changed in number and in morphology. But, the cells of the group treated with 18E6-2 siRNA were reduced in number and changed in morphology.

From the above results, it was confirmed that the siRNA of the present invention was successfully delivered by liposome.

EXAMPLE 9

Anticancer Effect on HeLa-Luc Cell Line

HeLa-Luc cell line was transfected with 18E6-1 siRNA or 18E6-2 siRNA in vitro. The cell line was cultured in DMEM (Sigma Chemical Co.) supplemented with 10% FBS at 37° C. with 5% $CO_2$ and 100% humidity. To the 6-well plate pre-inoculated with HeLa-Luc cells ($5\times10^4$ cells/well) 24 hours before was added siRNA for transfection (two times). The cell number and morphology were investigated on the $6^{th}$ day of transfection. The cells were recovered by treating with trypsin, stained with 0.3% trypan blue solution and counted with hemocytometer.

As a result, the cell number was decreased in HeLa-Luc cell line by the combination therapy with 18E6-1 siRNA, compared with the single therapy, which was consistent with the result shown in HeLa cell line (FIG. 21).

EXAMPLE 10

Experiment with Xenograft Model

To generate the cervix cancer xenograft model, $5\times10^6$ HeLa-Luc cells were injected subcutaneously into a 5 week old female balb-C nude mouse. 7 days later, tumor generation was confirmed. Then, the mouse was treated with siRNA (2 mg/kg) and cisplatin (0.5 mg/kg) every other day by taking turns, 7 times (intraperitoneal injection).

Isofluran was used as an anesthetic for in vivo imaging. Luciferase activity, which increases with the growth of a tumor, was measured 15 minutes after intraperitoneal injection of luciferin.

Bioluminescence signal released by luciferase was represented as the unit of photons/second/steradian/cm2, and the luciferase signal increases as the tumor grew.

After 2 weeks from the tumor growth, the changes of tumor size were observed. As a result, the tumor size was not much different among the no-treatment group and the single therapy groups each treated with low concentration of cisplatin, GFP siRNA and 18E6-1 siRNA. However, the tumor size was significantly reduced in the combination therapy group treated with 18E6-1 siRNA and low concentration of cisplatin, compared with the single therapy groups. The tumor size in this combination therapy group was also smaller than that of the combination therapy control group treated with GFP siRNA and low concentration of cisplatin (FIG. 22).

The tumor size was continuously measured in the combination therapy group. As a result, the tumor was constantly growing in the group treated with GFP siRNA and low concentration of cisplatin but was inhibited in the group treated with 18E6-1 siRNA and low concentration of cisplatin (FIG. 23).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A composition for the treatment of an HPV associated cancer comprising a first active part comprising a human papilloma virus (HPV) specific siRNA as an active ingredient; and a second active part comprising an anticancer agent at a low concentration as an active ingredient, wherein the HPV specific siRNA of the first active part comprises SEQ ID NO: 1.

2. The composition for the treatment of cancer according to claim 1, wherein the HPV specific siRNA of the first active part targets E6 protein gene.

3. The composition for the treatment of cancer according to claim 1, wherein the anticancer agent of the second active part is selected from the group consisting of cisplatin, heptaplatin, carboplatin and riboplatin.

4. The composition for the treatment of cancer according to claim 1, wherein the concentration of the anticancer agent is 0.625-160 μM.

5. The composition for the treatment of cancer according to claim 1, wherein the HPV specific siRNA of the first active part or the anticancer agent of the second active part is delivered by liposome.

6. The composition for the treatment of cancer according to claim 5, wherein the liposome comprises lipofectamine, oligofectamine, cationic lipid, lipid nanoparticles containing helper lipid for the purpose of enhancing intracellular delivery and having positive charge on their surfaces and 100-200 nm in particle size, or cationic polymers such as chitosan, polyethylenimine, polylysine and polyhistidine.

7. The composition for the treatment of cancer according to claim 1, wherein the HPV associated cancer is cervix cancer or head and neck cancer.

8. A method for preparing the composition of claim 1, comprising loading of the HPV specific siRNA or the anticancer agent to a liposome.

9. A method for treating an HPV associated cancer comprising the following steps:
 1) administering an effective dose of a HPV specific siRNA to a patient once or twice for 24 hours, wherein the HPV specific siRNA comprises SEQ ID NO: 1; and
 2) administering an effective dose of an anticancer agent at a low concentration to the patient for 4-7 days.

10. The method for treating cancer according to claim 9, wherein the HPV associated cancer is cervix cancer or head and neck cancer.

11. The method of claim 8, wherein the liposome comprises lipofectamine, oligofectamine, cationic lipid, lipid nanoparticles containing helper lipid for the purpose of enhancing intracellular delivery and having positive charge on their surfaces and 100-200 nm in particle size, or cationic polymers such as chitosan, polyethylenimine, polylysine and polyhistidine.

12. The method according to claim 9, wherein the HPV specific siRNA is administered at least twice at 12-48 hour intervals and then the anticancer agent is administered for 7 days.

* * * * *